United States Patent [19]

Yabe et al.

[11] Patent Number: 5,431,150
[45] Date of Patent: Jul. 11, 1995

[54] COVERED ENDOSCOPE HAVING A CAP COVER FOR SHIELDING A DILATION TUBE CAP WITH WHICH A DILATION TUBE IS COUPLED

[75] Inventors: Hisao Yabe, Hachioji; Yoshihiro Iida, Tama; Akira Suzuki; Hideo Ito, both of Hachioji; Yoshio Tashiro, Hino; Minoru Yamazaki; Osamu Tamda, both of Hachioji, all of Japan

[73] Assignee: Olympus Optical Co., Ltd., Tokyo, Japan

[21] Appl. No.: 24,082

[22] Filed: Mar. 1, 1993

[30] Foreign Application Priority Data

| Jan. 27, 1993 | [JP] | Japan | 5-001828 U |
| Jan. 27, 1993 | [JP] | Japan | 5-001829 U |
| Jan. 28, 1993 | [JP] | Japan | 5-001955 U |
| Jan. 28, 1993 | [JP] | Japan | 5-001956 U |

[51] Int. Cl.⁶ .............................. A61B 1/00
[52] U.S. Cl. ...................... 600/121; 600/104; 600/157; 600/158
[58] Field of Search .................. 128/4, 10, 6

[56] References Cited

U.S. PATENT DOCUMENTS

| 4,646,722 | 3/1987 | Silverstein et al. | 128/4 |
| 4,907,395 | 3/1990 | Opie et al. | 128/4 X |
| 4,972,825 | 11/1990 | Vescovo, Jr. | 128/10 |
| 4,991,564 | 2/1991 | Takahashi et al. | 128/4 |
| 5,050,585 | 9/1991 | Takahashi | 128/4 |
| 5,154,166 | 10/1992 | Chikama | 128/4 |

FOREIGN PATENT DOCUMENTS 325138 11/1992 Japan .................. 128/4

Primary Examiner—Richard J. Apley
Assistant Examiner—Beverly A. Meindl
Attorney, Agent, or Firm—Armstrong, Westerman, Hattori, McLeland & Naughton

[57] ABSTRACT

An endoscope cover-sheathed endoscope is composed of an endoscope having an elongated insertional part that is inserted into a living body, and an endoscope cover including an insertional part cover in which an endoscope insertion channel into which the elongated insertional part is inserted is formed. A tube cap with which the terminal of a tube, which communicates with the endoscope insertion channel and feeds air to the endoscope insertion channel in order to enable insertion or removal of the insertional part into or from the endoscope insertion channel, is coupled is shielded with a cap cover, thus preventing spread of contamination.

4 Claims, 27 Drawing Sheets

COVERED ENDOSCOPE HAVING A CAP COVER FOR SHIELDING A DILATION TUBE CAP WITH WHICH A DILATION TUBE IS COUPLED

BACKGROUND OF THE INVENTION

1. Field of the Invention

The present invention relates to a covered endoscope having a dilation tube coupled to a dilation tube cap, where the cap is shielded with a cap cover.

2. Description of the Related Art

Endoscopes have been widely adopted in the field of medicine in recent years. When an endoscope for a medical use is inserted into a living body, body fluid or the like sometimes adheres to an observation window formed at the distal end of an insertional part, and disables clear observation. To overcome this drawback, an air supply channel or a water supply channel is incorporated so that the body fluid or the like adhering to the observation window can be removed by spraying fluid on the observation window using a hand-held operational device. Some endoscopes are provided with a suction channel for sucking unnecessary body fluid or the like and discharging it.

Some endoscopes have a forceps (treatment adaptor) channel in order to enable collection of tissues using biopsy forceps or treatment using treatment adaptors.

In an endoscope having a channel such as the foregoing air supply channel or forceps channel, after the endoscope is applied to a patient, cleaning or disinfection is carried out in order to prevent infection. It takes, however, excessive time to achieve perfect cleaning or disinfection, which deteriorates the use efficiency of an endoscope. Another problem is that disinfection work is cumbersome.

An endoscope cover-sheathed endoscope has been proposed accordingly, wherein an endoscope itself is sheathed with an endoscope cover and then put to use. A used endoscope is kept out of dirt and need not be cleaned or disinfected.

For example, U.S. Pat. No. 4,991,565 has disclosed a cover for sheathing an insertional part of an endoscope, wherein an insertional endoscope part is inserted into the cover (or sheath). In an effort to simplify insertion or removal of the insertional endoscope part into or from the cover, air is fed from a dilator to the cover into which the insertional endoscope part is inserted, thus dilating the cover.

The cover is, therefore, provided with a dilation tube cap for guiding the air drawn with the dilator to the portion into which the insertional endoscope part is inserted. A dilation tube is coupled with the dilation tube cap, and the cover is dilated with the air supplied from the cover dilator. This permits easy sheathing.

A flange is formed on the dilation tube cap so that when the distal end of the dilation tube is coupled with the dilation tube cap in such a manner that the distal end shields the tube cap, the dilation tube will not come off.

When an endoscope is unsheathed from the cover, however, the cover becomes contaminated with body fluid or the like in a body cavity. The dilation tube cap formed on the cover also becomes contaminated. The dilation tube also gets contaminated when coupled with the dilation tube cap.

When the endoscope is sheathed with a new cover using the dilation tube, the portion of the dilation tube coupled with and brought into contact with the dilation tube cap gets contaminated. When a glove touches the contaminated dilation tube cap, the entire cover gets contaminated via the glove.

SUMMARY OF THE INVENTION

An object of the present invention is to provide a covered endoscope permitting reliable prevention of the spread of contamination through a dilation tube cap.

Another object of the present invention is to provide a covered endoscope permitting effortless prevention of spread of contamination through a dilation tube cap.

The present invention comprises an endoscope cover having a dilation tube cap with which an end of a dilation tube extending from an endoscope cover dilator is coupled, and an endoscope cover-sheathed endoscope.

A cover member for shielding the dilation tube cap is included to prevent the dilation tube cap from being contaminated with a contaminated glove or the like during endoscopic examination. This prevents contamination of a dilation tube to be coupled with the dilation tube cap, and eventually permits reliable prevention of spread of contamination.

BRIEF DESCRIPTION OF THE DRAWINGS

FIGS. 1 to 8 relate to the first embodiment of the present invention;

FIG. 1 is a general oblique view of a configuration of a covered endoscope system;

FIG. 2 is a partial cross-sectional view of a structure of a covered endoscope;

FIG. 3 shows an insertional part cover and a coverable endoscope;

FIG. 4 shows an 4—4 cross section of FIG. 3;

FIG. 5 shows a 5—5 cross section of FIG. 3;

FIG. 7 is a schematic diagram showing a structure of a cover dilator;

FIG. 8 is an oblique view showing a holder of a cover holding instrument holding an insertional part cover;

FIG. 10 is an explanatory diagram showing an operational part cover covering a dilation tube cap;

FIG. 11 is an explanatory diagram of an arrangement for holding an insertional part cover by inserting a holder formed on the insertional part into an attachment port of a cover holding instrument;

FIG. 12 is an explanatory diagram of a dilation tube cap coupled with a dilation tube via a cover holding instrument;

FIG. 13 is a schematic diagram of a composition of a fluid control;

FIG. 15 is a general oblique view showing a configuration of a covered endoscope system;

FIG. 16 is a partial cross-sectional view of a major portion of a covered endoscope;

FIG. 17 shows a 17—17 cross-section of FIG. 16 and an insertional part cover;

FIG. 18 is a schematic diagram of a composition of a cover dilator;

FIG. 19 is a side view showing a dilation tube for linking a cover dilator with a dilation tube cap;

FIG. 21 is a cross-sectional view of a major portion of a covered endoscope;

FIG. 22 shows a 22—22 cross section of FIG. 21 and an insertional part cover;

FIG. 23 is a side view of a coverable endoscope;

FIG. 24 is a cross-sectional view of a waterproof cap;

FIG. 25 shows a cover dilator linked with a connector of a coverable endoscope via a dilation tube;

FIG. 26 is a general oblique view of a configuration of a covered endoscope system;

FIG. 27 is a cross-sectional view of a structure of a covered endoscope;

FIG. 28 is a cross-sectional view of a joint of a dilation tube coupled with a cover dilator and a dilation tube cap;

FIG. 30 is a general oblique view of a configuration of a covered endoscope system;

FIG. 31 is a partial cross-sectional view of a structure of a major portion of a covered endoscope;

FIG. 36 is a partial cross-sectional view of a structure of a major portion of a covered endoscope;

FIG. 37 is a partial cross-sectional view of a structure of a major portion of a covered endoscope; and FIG. 38 is a partial cross-sectional view of a structure of a major portion of a covered endoscope.

DETAILED DESCRIPTION OF THE PREFERRED EMBODIMENTS

Embodiments of the present invention will be described with reference to the drawings.

Figure 1:
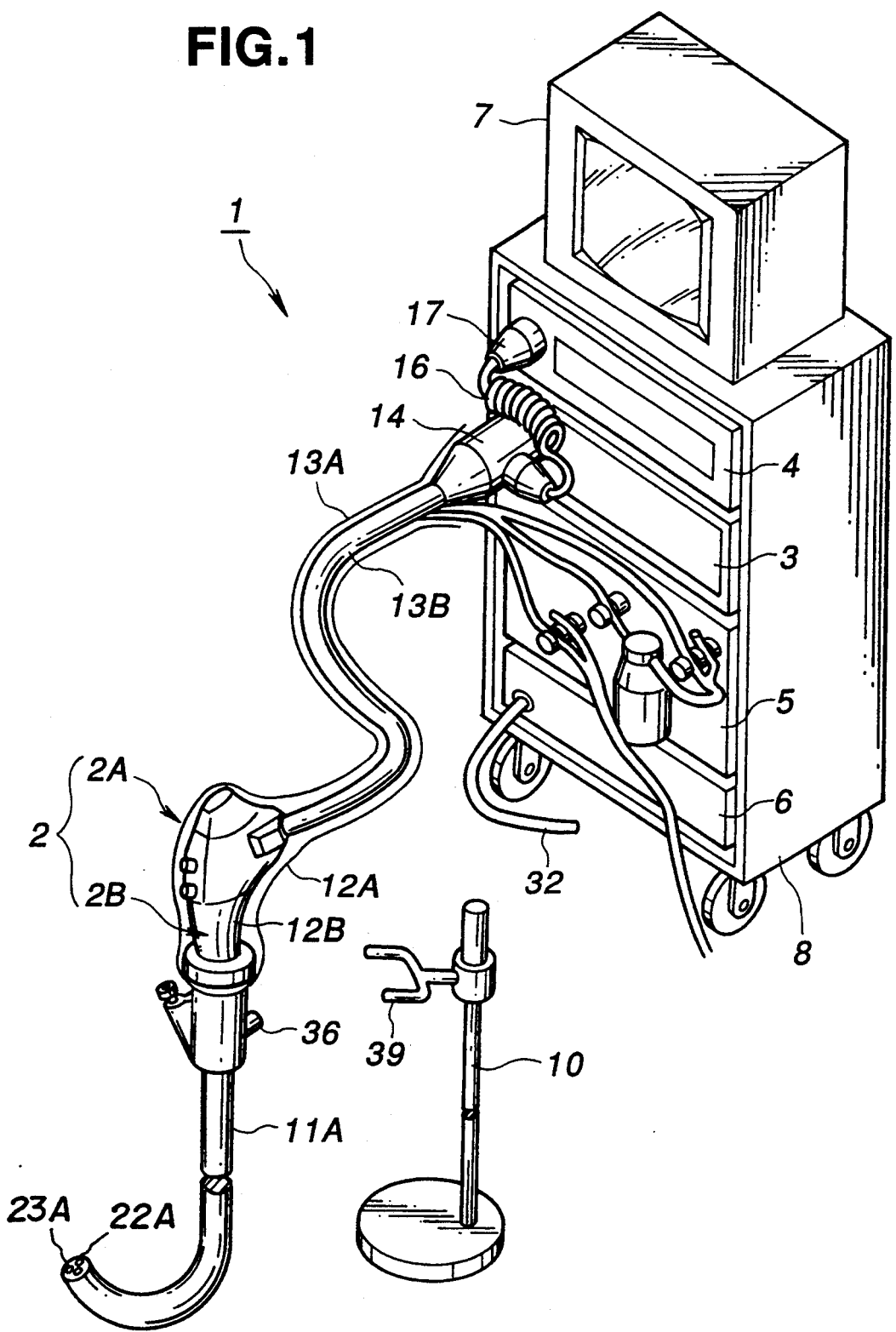

As shown in FIG. 1, a covered endoscope system 1 comprises a channeled and endoscope-cover sheathed endoscope (hereafter, covered endoscope), which is made up of a channeled endoscope cover (hereafter, cover) 2A and a coverable endoscope 2B which is sheathed with the cover 2A, a light source apparatus 3 for supplying illumination light to the coverable endoscope 2B, a video processor 4 that performs signal processing for an imaging means incorporated in the coverable endoscope 2B, a fluid control apparatus 5 for supplying air or water through a tube running in the cover 2A, a channeled endoscope cover dilator 6 (hereafter, cover dilator) for use in sheathing the coverable endoscope 2B with the cover 2A, and a monitor 7 for displaying a video signal processed by the video processor 4. The light source apparatus 3, video processor 4, fluid control apparatus 5, and cover dilator 6 are mounted in a cart 8, and the monitor 7 is placed on the top of the cart 8.

Figure 2:
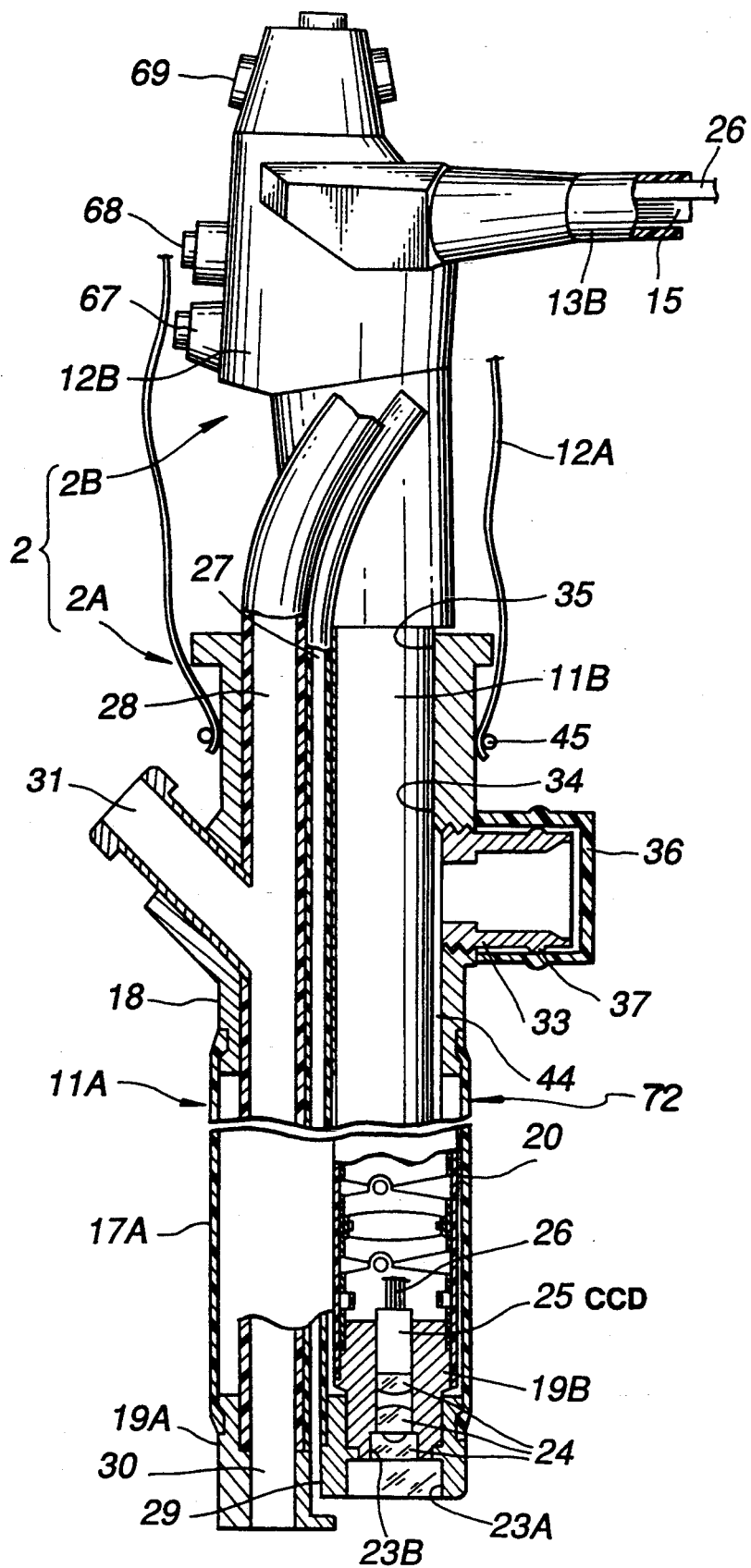
Figure 3:
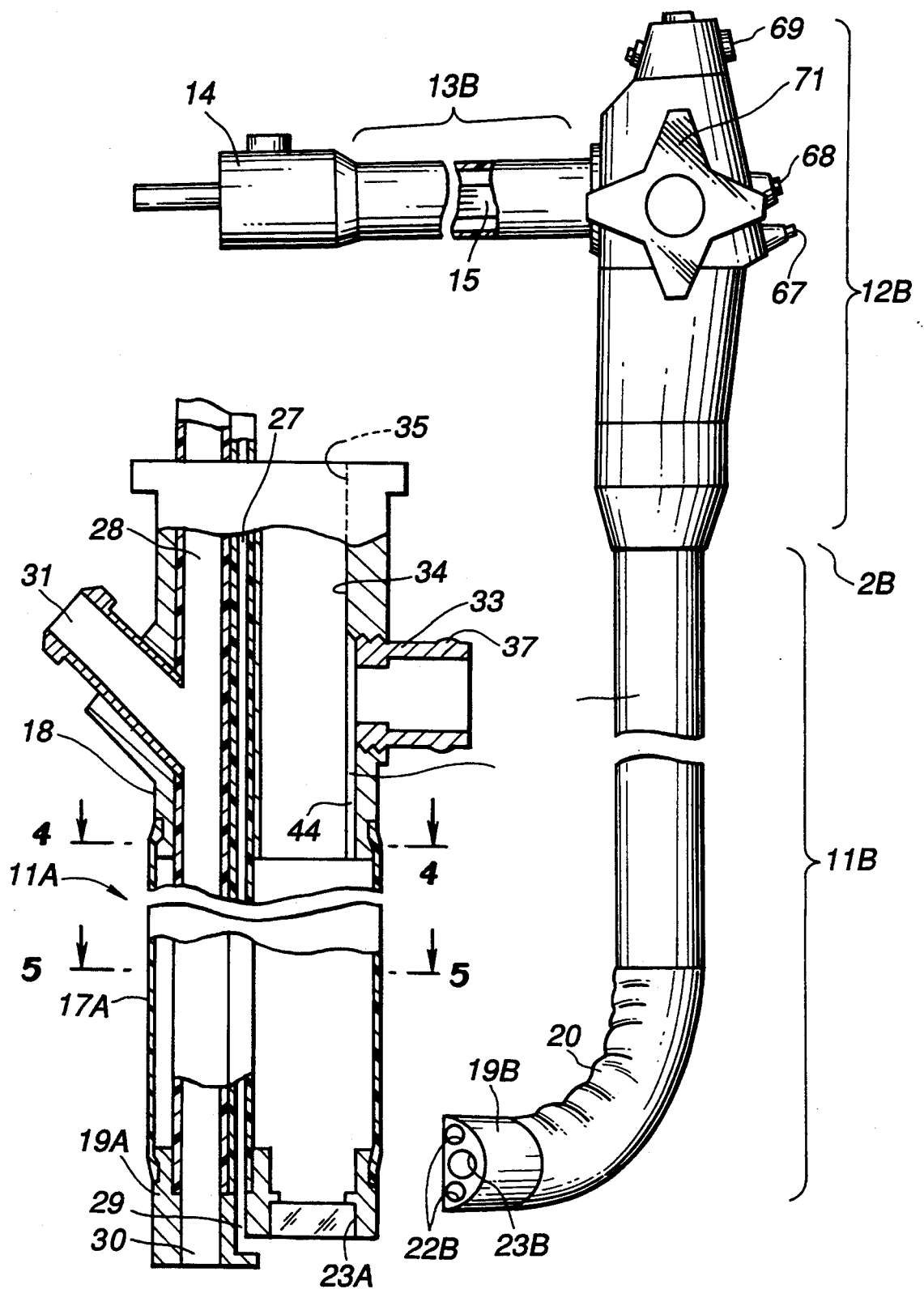

FIG. 2 is an enlarged view of the covered endoscope 2 of FIG. 1. For endoscopic examination, the clean coverable endoscope 2B is sheathed with the clean cover 2A. After the endoscopic examination, the cover 2A is disposed of, while the coverable endoscope 2B is sheathed with a new clean cover 2A and reused. FIG. 3 shows an insertional part cover 11A of the cover 2A and the coverable endoscope 2B sheathed with the insertional part cover 11A separately.

When the coverable endoscope 2B is sheathed with the insertional part cover 11A that is part of the cover 2A, or when the sheathed coverable endoscope 2B is unsheathed, a cover holding instrument 10 shown in FIG. 1 is used to hook the proximal end of the cover 2A onto the cover holding instrument 10, and then an insertional endoscope part 11B of the coverable endoscope 2B is inserted or extracted.

The coverable endoscope 2B comprises the insertional endoscope part 11B (hereinafter, insertional part) that is elongated and flexible, and an operational endoscope part 12B (hereinafter, operational part) formed at the proximal end of the insertional part 11B, and a universal cord 13B extending from the side of the operational part 12B. A connector 14 attached to the terminal of the universal cord 13B can be linked with the light source apparatus 3 so as to be freely detachable. When the connector 14 is connected to the light source apparatus 3, illumination light originating from a lamp in the light source apparatus 3 is supplied to the terminal of a light guide 15 (See FIG. 2).

The insertional part 11B is composed of a flexible portion 72 that is flexible and elongated, a bending section 20 formed at the distal end of the flexible portion 72, and a distal end 19B formed at the distal end of the bending section 20. The bending section 20 can be bent by operating an angulation knob 71 formed on the operational part 12B.

The operational part 12B is provided with, for example, an air/water supply switch 67, a suction switch 68, and a freeze switch 69. By operating the switches, air/water supply, suction, and image freezing can be performed.

The connector 14 is linked with a cable 16. A signal connector 17 at the terminal of the cable 16 can be freely connected or disconnected to or from the video processor 4.

The cover 2A consists of an insertional part cover 11A, an operational part cover 12A, and a universal cord cover 13A, which sheath the insertional part 11B of the coverable endoscope 2B, operational part 12B thereof, and universal cord 13B thereof respectively.

The insertional part cover 11A is made up of an insertional part cover skin 17A for sheathing the insertional part 1B, an operational part locking cap 18 airtightly attached to the proximal end of the insertional part cover skin 17A, and a cover distal end 19A airtightly attached to the terminal of the insertional part cover skin 17A.

The insertional part cover skin 17A of the cover 2A is made of, for example, a thin synthetic resin containing polyurethane, polyester, silicon, and other substances, and has flexibility and stretchability. The insertional part cover skin 17A can, therefore, be dilated by feeding air to the insertional part cover skin 17A through a dilation tube cap 33 to be described later. This makes it easy to insert or remove the coverable endoscope 2B.

The operational part cover 12A and universal cord cover 13A are also made of a thin synthetic resin containing polyurethane and other substances.

The operational part locking cap 18 and cover distal end 19A may be made of a synthetic resin or a metal.

Illumination light that originates from a lamp, which is not shown, in the light source apparatus 3 and enters the terminal surface of the universal cord 13B sheathing the light guide 15 is transmitted by the light guide 15, and then emitted forward from an end surface attached to an illumination window 22B of the distal end 19B of the insertional part 11B through a transparent plate of a cover illumination window 22A (See FIG. 1) opposed to the end surface to a subject.

The illuminated subject such as a lesion reflects light which forms an optical image on a focal surface of an objective optical system 24 through a transparent plate of a cover observation window 23A adjacent to the cover illumination window 22A and through the objective optical system 24 attached to an observation window 23B opposed to and located inside of the cover observation window 23A.

A CCD 25 is arranged on the focal surface of the objective optical system 24, which photoelectrically transforms the optical image. Then, the resultant signal passes through a signal cable 26 running through the insertional part 11B and universal cord 13B, and the signal cable 16, and then enters the video processor 4. After signal processing, a standard video signal is produced. The video signal is input to the monitor 7 and displays an image of the subject on a screen.

As shown in FIGS. 2, 3, 4, and 5, the insertional part cover 11A is provided with an air/water supply tube and a suction tube. For the air/water supply tube and suction tube, an air/water supply channel 27 and a suction channel 28 are formed. The distal end of the air/water supply channel 27 communicates with a nozzle 29 of the cover distal end 19A. The distal opening of the nozzle 29 is facing the outer surface of the cover observation window 23A.

The proximal end of the air/water supply tube is extended above the operational part locking cap 18, and routed to the fluid control apparatus 5 while being sheathed together with the universal cord 13B by the universal cord cover 13A. Then, the proximal end of the air/water supply tube is bifurcated into an air supply tube and a water supply tube which are linked with an air pipe and a water pipe lying in the fluid control apparatus 5. Even when body fluid or the like adheres to the cover observation window 23A, it can be removed by supplying air or water through the air/water supply channel 27.

A forceps insertion port 31, and a dilation tube cap 33 with which a dilation tube 32 connected to the cover dilator 6 is coupled are formed on the side of the operational part locking cap 18.

The forceps insertion port 31 joins the suction channel 28 and opens at a forceps exit 30, which also serves as a suction port, in the cover distal end 19A.

The dilation tube cap 33 is separated by 90° or more in the radial direction from the forceps insertion port 31.

The top of the operational part locking cap 18 has an opening 35 of an endoscope insertion channel 34 into which the insertional part 11B of the coverable endoscope 2B is inserted (mounted). The endoscope insertion channel 34 is the portion of the internal space enclosed by the cover distal end 19A, insertional part cover skin 17A, and operational part locking cap 18 excluding the air/water supply channel 27 and suction channel 28, into which the coverable endoscope 2B is inserted.

The endoscope insertion channel 34 externally opens onto the outside at the opening 35 that is formed at the proximal end of the endoscope insertion channel 34 and through which the insertional part 11B is inserted, and at the dilation tube cap 33 with which the dilation tube 32 is coupled. The other portion of the endoscope insertion channel 34 is not exposed to the outside. When the insertional part 11B is inserted, therefore, the insertional part 11B is not exposed to the outside.

Figure 4:
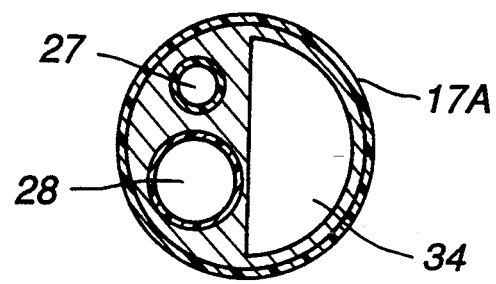
Figure 5:
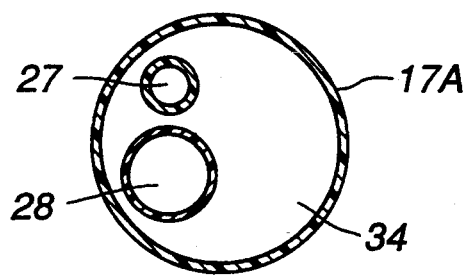

In this embodiment, as apparent from FIGS. 4 and 5, the endoscope insertion channel 34 on the side of the operational part locking cap 18 has a semi-circular cross section similar to that of the insertional part 11B of the coverable endoscope 2B.

Figure 6A:
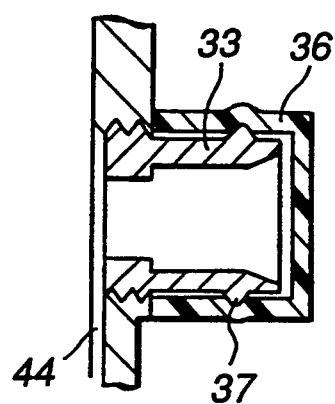
FIGS. 6a and 6b are cross-sectional views showing a dilation tube cap cover for covering a dilation tube cap.

The opening 35 of the endoscope insertion channel 34 bored on the operational part locking cap 18 communicates with the dilation tube cap 33. The dilation tube cap 33 is shielded with a tubular dilation tube cap cover 36 whose bottom is usually blocked as shown in FIGS. 2 and 6a, thus protecting the dilation tube cap 33 from dirt. The dilation tube cap cover 36 is made of a resin or realized with an elastic member.

A projection 37 is formed on the outer circumference of the dilation tube cap 33, and helps attach the dilation tube cap cover 36 to prevent it from coming off.

Figure 6B:
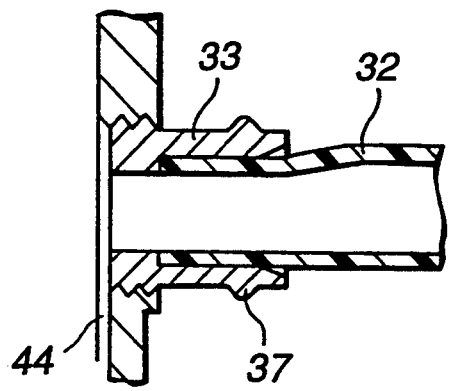

When the coverable endoscope 2B is inserted into the insertional part cover 11A, the dilation tube cap cover 36 is removed and the terminal of the dilation tube 32 is coupled with the dilation tube cap 33 as shown in FIG. 6b.

Figure 8:
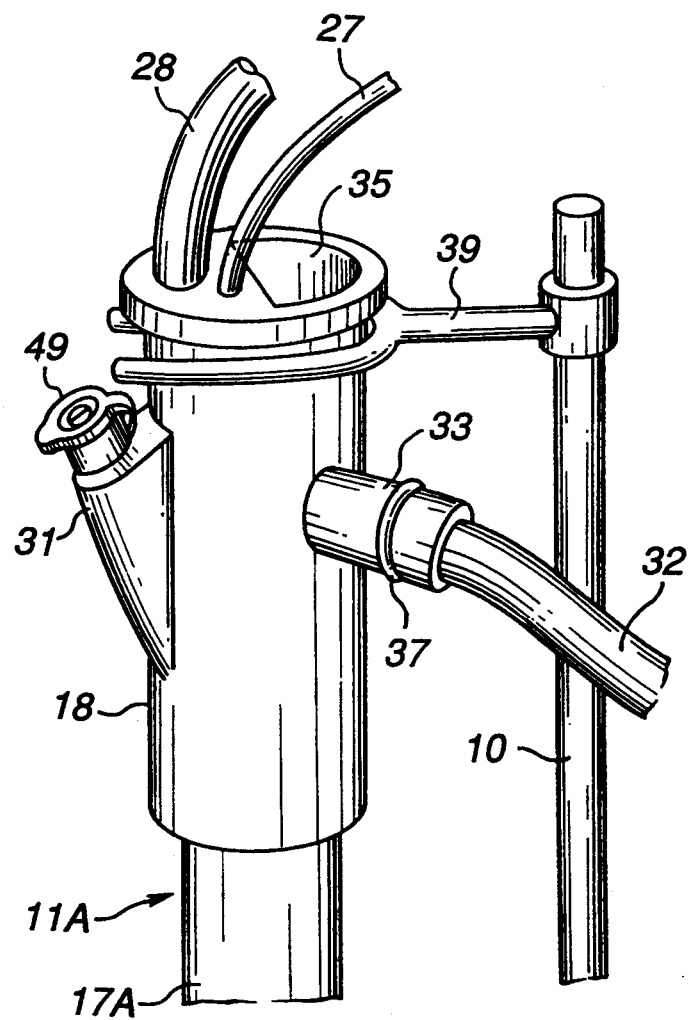

In this case, as shown in FIG. 8, a flange at the upper end of the operational part locking cap 18 is held by a semi-circular holder 39 attached to the cover holding instrument 10, and then the insertional part 11B of the coverable endoscope 2B is inserted through the opening 35 bored on the top of the operational endoscope part locking cap 18. Thus, the coverable endoscope 2B is mounted in the endoscope insertion channel 34 effortlessly.

Figure 7:
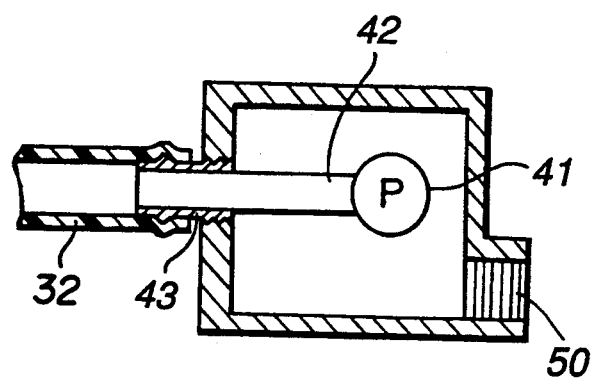

FIG. 7 shows a structure of a cover dilator 6 schematically. The cover dilator 6 consists basically of an air pump 41 and an air supply channel 42. An open end of the air supply channel 42 is provided with a base 43 with which the proximal portion of the dilation tube 32 is coupled. The cover dilator 6 keeps supplying air constantly. When the function of the cover dilator 6 is unused, as shown in FIG. 1, the terminal of the dilation tube 32 is uncoupled with the dilation tube cap 33 and communicating with the outside air.

As shown in FIG. 7, a disinfection filter 50 is installed in the portion of the housing of the cover dilator 6 leading to an opening. The disinfection filter 50 disinfects the outside air to be supplied to the pump 41. Thus, the air supplied through the endoscope channel 34 is the air passed through the disinfection filter 50, and is always clean.

When the coverable endoscope 2B is inserted into the insertional part cover 11A, as shown in FIG. 6b, the terminal of the dilation tube 32 is pushed into the dilation tube cap 33 so that the dilation tube 32 will be airtightly fitted into the dilation tube cap 33. Then, air drawn with the air pump 41 is fed to the endoscope insertion channel 34 via the dilation tube cap 33, and dilates the endoscope insertion channel 34. This permits effortless insertion of the insertional part 11B.

As shown in FIGS. 2, 6a, and 6b, a notch 44 is formed longitudinally in the portion of the endoscope insertion channel 34 around and below (toward a cover distal end 19A) the area communicating with the dilation tube cap 33. When the insertional part 11B is inserted, the notch 44 guides air supplied through the dilation tube cap 33 toward the distal end 19A.

The portion of the endoscope insertion channel 34 above the area communicating with the dilation tube cap 33 does not have the notch 44, whose cross section substantially agrees with that of the insertional part 11B.

When the insertional part 11B is inserted through the opening 35 formed at the upper end of the endoscope insertion channel 34, air supplied through the dilation tube cap 33 flows down from the notch 44 that appears as a dent in the proximal portion of the cap 33, because the notch 44 provides a passage of air. That is to say, the endoscope insertion channel 34 is dilated to permit effortless insertion of the insertional part 11B. As for removal, the insertional part 11B can also be removed effortlessly.

When the insertion of the insertional part 11B is completed, the terminal of the dilation tube 32 is decoupled from the dilation tube cap 33. The dilation tube cap 33 is, as shown in FIGS. 2 and 6a, shielded with the dilation tube cap cover 36 so that the dilation tube cap 33 will not be contaminated.

An opening of an operational part cover 12A is, as shown in FIG. 2, secured with an elastic ring 45, which stretches in the radial direction, at a position below the flange formed at the upper end of the operational part locking cap 18. The other opening of the operational part cover 12A on the side of the universal cord cover 13A is united with the universal cord cover 13A and opens onto a connector 14.

As shown in FIG. 8, the forceps insertion port 31 is covered with a forceps cock 49. When used, forceps are inserted to push a slit apart.

Next, the operation of the first embodiment will be described.

When the coverable endoscope 2B is inserted into (sheathed with) the insertional part cover 11A of the cover 2, as shown in FIG. 8, the semi-circular holder 39 attached to the cover holding instrument 10 is used to hold the flange formed at the upper end of the operational part locking cap 18.

Then, the terminal of the dilation tube 32 is coupled with the dilation tube cap 33, whereby air is fed from the cover dilator 6 to the endoscope insertion channel 34. The air leaks to the outside through the opening 35.

When the insertional part 11B of the coverable endoscope 2B is inserted through the opening 35, the opening 35 is almost blocked. Air is fed to the insertional part cover skin 17A through the notch 44, and thus internally pressurizes the insertional part cover skin 17A having stretchability. Consequently, the insertional part cover skin 17A is dilated to enable smooth insertion of the insertional part 11B.

When the insertion is completed, the terminal of the dilation tube 32 is decoupled from the dilation tube cap 33. Then, air leaks out from the dilation tube cap 33. The insertional part cover skin 17A shrinks due to its own elasticity (the outer diameter of the insertional part cover skin 17A diminishes). The outer surface or the skin of the insertional part 11B almost adheres to the inner surface of the insertional part cover skin 17A.

After the terminal of the dilation tube 32 is decoupled, the dilation tube cap cover 36 is attached to the dilation tube cap 33 in order to shield the dilation tube cap 33. Thereby, endoscopic examination is enabled, and can be performed in the same manner as using a normal endoscope.

During endoscopic examination, if an operator's hand or glove contaminated by applying the endoscope to a patient touches the dilation tube cap 33 accidentally, since the dilation tube cap 33 is shielded with the dilation tube cap cover 36, the dilation tube cap 33 itself can be prevented from being contaminated.

Therefore, after examination is completed, when the insertional part 11B is unsheathed from the insertional part cover 11A, even if the dilation tube 32 is re-coupled with the dilation tube cap 33, the dilation tube 32 will not be contaminated.

When another new insertional part 11B is inserted into a new insertional part cover 11A in order to perform endoscopic examination on another patient, even if the dilation tube 32 is reused and coupled with the dilation tube cap 33 of the new insertional part cover 11A, the dilation tube cap 33 will by no means be contaminated.

After endoscopic examination is completed, the cover 2A is disposed of and the used coverable endoscope 2B is cleaned.

On the contrary, if the dilation tube cap 33 is not covered like that in a prior art, while a patient is being treated, an operator's hand or fingers may touch the dilation tube cap 33 accidentally. Then, if the dilation tube 32 is coupled with the dilation tube cap 33, contamination spreads to the dilation tube 32. If the same dilation tube 32 is coupled with a new dilation tube cap 33, the new dilation tube cap 33 will be contaminated. A hand engaged in the connection will also be contaminated. The hand may spread contamination to other parts of the cover 2A. This eventually causes another patient to contract infection.

According to this embodiment, spread of contamination can be prevented reliably. Occurrence of infection can, therefore, be reliably prevented.

In this embodiment, various channels (disposed of after examination) required to realize endoscopic functions necessary for endoscopic examination; such as, air/water supply, suction, and forceps treatment functions are formed in the cover 2A but not formed in the coverable endoscope 2B which is inserted into the cover for use.

When the coverable endoscope 2B is cleaned or disinfected in order to make the coverable endoscope 2B clean, only a short period of time is required to attain perfect cleanliness.

An endoscope used in conjunction with the cover 2A is not limited to the dedicated coverable endoscope 2B that is shaped in conformity with the cover 2A. A normal endoscope which is used without the cover 2A or with a bare body is also usable.

Figure 9:
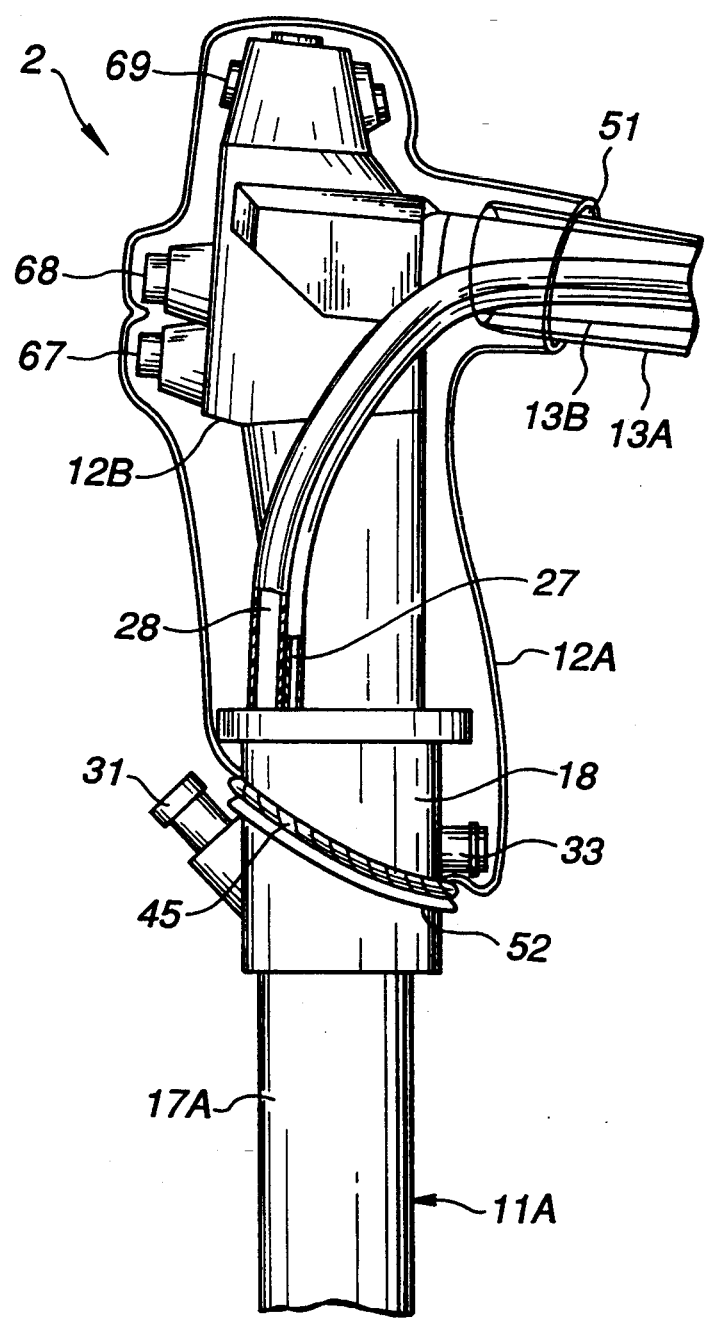
FIG. 9 is an explanatory diagram showing an operational part cover covering a dilation tube cap according to a second embodiment of the present invention.

FIG. 9 shows a major portion of a covered endoscope 2 in the second embodiment of the present invention. In this embodiment, an operational part cover 12A is a sack-like member made of a soft high polymer material, having a universal cord opening 51 through which a universal cord 13B, and an air/water supply tube or a suction tube are passed, and an endoscope opening 52 through which an operational part 12B of a coverable endoscope 2B and an operational part locking cap 18 (of an insertional cover 11A) are put in the operational part cover 12A.

The proximal end of a universal cord cover 13A is fitted into the universal cord opening 51.

The operational part cover 12A sheathes the operational part 12B of the coverable endoscope 2B from the vicinity of the proximal end of the universal cord 13B to the upper area of the operational part locking cap 18 including a dilation tube cap 33. The endoscope opening 52 is secured on the outer circumferential surface of the operational part locking cap 18 using an elastic ring 45 that stretches in the radial direction.

As described above, the dilation tube cap 33 is shielded with the operational part cover 12A. In this embodiment, a dilation tube cap cover is not employed.

In this embodiment, the elastic ring 45 is hooked on the side of the dilation tube cap 33 facing an insertional part cover skin 17A and on the side of the forceps insertion port 31 facing the operational part 12B of the coverable endoscope 2B, whereby the operational part cover 12A is attached to the coverable endoscope 2B. According to this embodiment, the dilation tube cap 33 is shielded with the operational part cover 12A.

The dilation tube cap 33 can also be shielded merely by attaching the operational cover 12A to the coverable endoscope 2B. This improves working efficiency. The dilation tube cap cover in the first embodiment is unnecessary, which reduces the number of parts and lowers prime cost.

Figure 10:
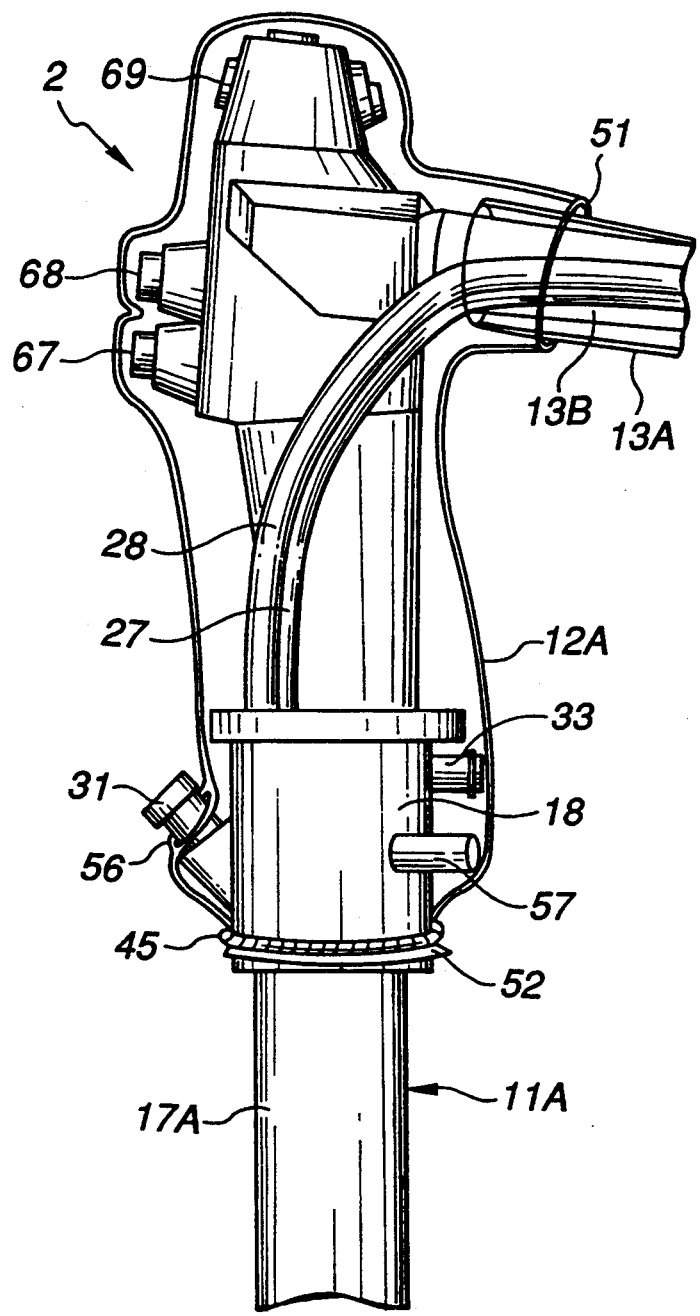
FIGS. 10 and 11 relate to a third embodiment of the present invention.

FIG. 10 shows a major portion of a covered endoscope 2 in the third embodiment of the present invention. In this embodiment, an operational part cover 12A is a sack-like member made of a soft high polymer material. Similarly to the second embodiment, the operational part cover 12A has a universal cord opening 51 and an endoscope opening 52. An elastic ring 45 capable of stretching in the radial direction is used to secure the endoscope opening 52 on the outer circumferential surface near the lower end of an operational part locking cap 18.

The terminal of a universal cord cover 13A is fitted into the universal cord opening 51.

The operational part cover 12A further includes a forceps insertion opening 56 through which an end of a forceps insertion port 31 is exposed and forceps are inserted. The operational part cover 12A shields all parts of an operational part except this end.

Figure 11:
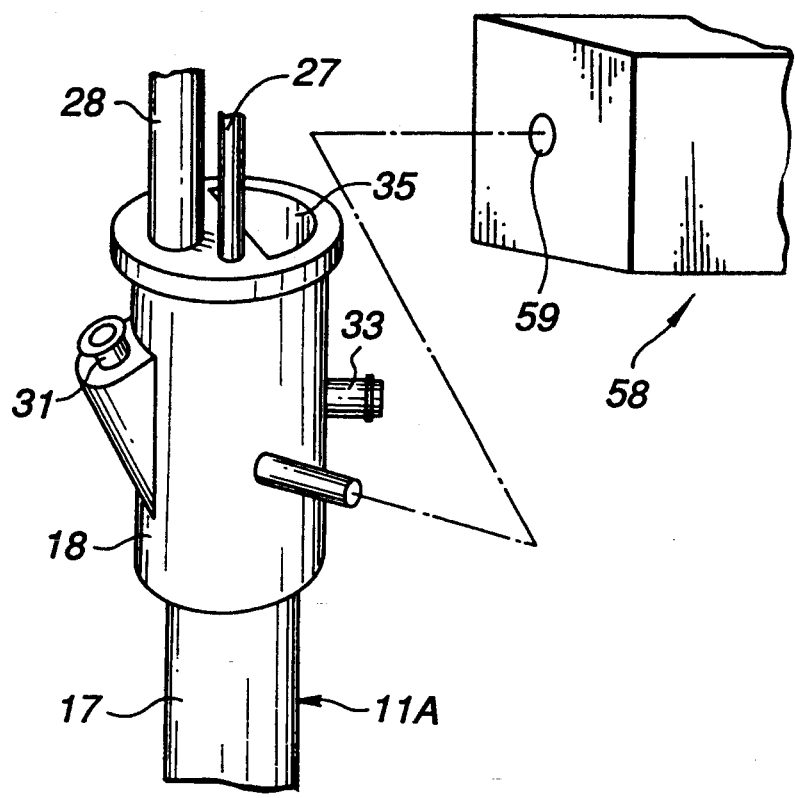

In this embodiment, a bar-shaped holder 57 is formed on the side of the operational part locking cap 18. The holder 57 is, as shown in FIG. 11, inserted into an attachment port 59 of a cover holding instrument 58 and thus holds on to an insertional part cover 11A.

In the first embodiment, as shown in FIG. 8, the semicircular holder 39 is attached to the cover holding instrument 10 and the flange is formed on the operational part locking cap 18, whereby the insertional part cover 11A is held by the cover holding instrument 10. In this embodiment, the insertional part cover 11A has the holder 57 which is inserted into the attachment port 59 bored on the cover holding instrument 58, whereby the insertional part cover 11A is held by the cover holding instrument 58. The holder 57 is shielded with the operational part cover 12A so as not to be contaminated.

The foregoing structure makes it possible to replace the holder 57 at the same time when the insertional part cover 11A is renewed, which improves working efficiency.

In a prior art, when the insertional part cover 11A is detached from the coverable endoscope 2B, the coverable endoscope has been used. The insertional part cover 11A is, therefore, contaminated with body fluid or the like. The holder holding the contaminated insertional part cover 11A is also contaminated.

When the contaminated holder is used to sheath the coverable endoscope 2B with a new insertional part cover 11B, the insertional part cover 11B which must be clean is contaminated via the holder. If the contaminated insertional part cover 11B is used, there is a fear of patient infection. In the prior art, therefore, when the insertional part cover 11B is replaced, the holder also must be replaced.

In this embodiment, since the holder 57 is formed on the operational part locking cap 18 of the operational part cover 11B, when the insertional part cover 11A is renewed, the holder 57 can also be replaced. This improves working efficiency.

In this embodiment, as shown in FIG. 10, the forceps insertion opening 56 is aligned with the forceps insertion port 31, and then the operational part cover 12A is attached to the coverable endoscope 2B. The operational part cover 12A shields the operational part locking cap 18.

According to this embodiment, since the operational part cover 12A shields the operational part locking cap 18, whatever positional relationship is born by the forceps insertion port 31, dilation tube cap 33, and holder 57, the dilation tube cap 33 and holder 57 can be shielded by the operational part cover 12A.

The above structure can prevent a hand or fingers from touching not only the dilation tube cap 33 but also the holder 57, which reliably prevents spread of contamination.

In the aforesaid third embodiment, the dilation tube cap 33 may be shaped for engagement with the attachment port 59. Then, the dilation tube cap 33 is engaged with the attachment port 59 of the cover holding instrument 58, so that the cover holding instrument 58 can hold on to the insertional part cover 11A.

The above structure obviates the holder 57, which makes it easy to mold the operational part locking cap 18.

Figure 12:
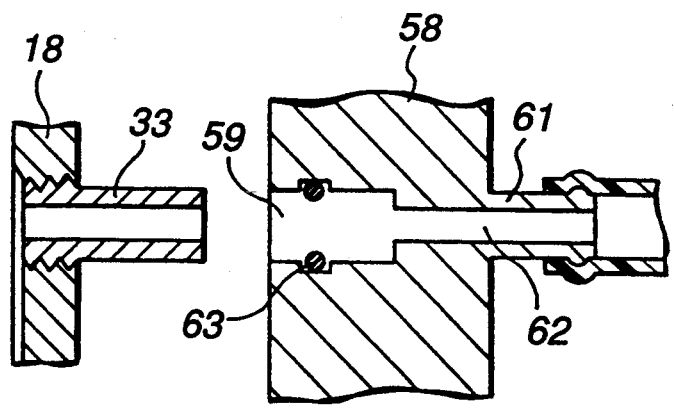
FIGS. 12 and 13 relate to a fourth embodiment of the present invention.

FIG. 12 shows a major portion of the fourth embodiment of the present invention. In this embodiment, a dilation tube 32 is coupled with a dilation tube cap 33 via an attachment port 59 formed in a holding instrument 58.

The cover holding instrument 58 has not only the attachment port 59 but also a joint 61. The terminal of the dilation tube 32 is linked with the joint 61. The joint 61 communicates with the attachment port 59 via an air pipe 62 running through the holding instrument 58.

An elastic ring 63 is attached to the inside of the attachment port 59, which helps airtightly couple the attachment port 59 with the dilation tube cap 33.

Figure 13:
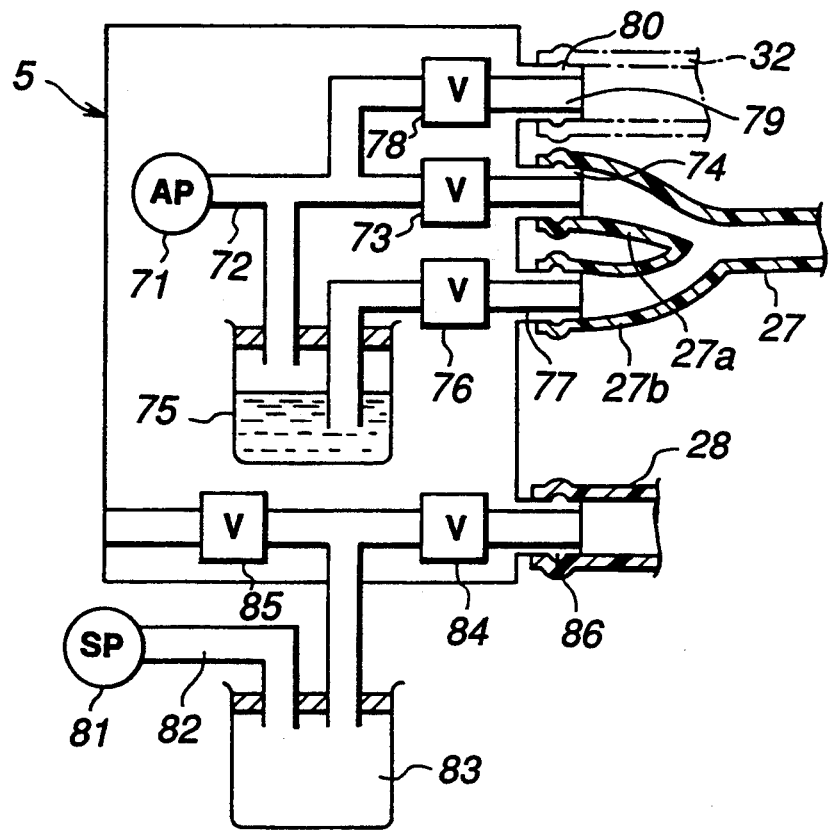

In this embodiment, a fluid control apparatus 5 has a composition shown in FIG. 13 and also functions as a cover dilator 6. This embodiment, therefore, obviates the cover dilator 6 shown in FIG. 1.

For air or water supply, an air pump 71 is, as indicated with solid lines, connected to an air joint 74 to be linked with the proximal end of an air tube 27a, which is one of two branches of a bifurcated air/water supply channel 27, via a pipe 72 and an electromagnetic valve 73 attached to a pipe branching out from pipe 72.

The air pump 71 is connected to a water joint 77 to be linked with the proximal end of a water tube 27b, which is the other one of the branches of the bifurcated air/water supply channel 27, via a water tank 75 installed in the middle of a pipe branching out from the pipe 72 and an electromagnetic valve 76.

The air pump 71 is connected to a leakage pipe 79, which opens onto the outside air, via an electromagnetic valve 78 attached to a pipe branching out from the pipe 72.

A suction pump 81 is connected to electromagnetic valves 84 and 85, which are attached to the respective branches of a bifurcated pipe, via a sucked object storage tank 83 installed in the middle of a pipe 82. The electromagnetic valve 84 is connected to a joint 86 which is linked with the proximal end of a suction channel 28, while the electromagnetic valve 85 joins the atmosphere.

In this embodiment, a joint 80 is formed at an end of the leakage pipe 79 so that the air pump 71 can be used as a cover dilator. The joint 80 can be linked with the terminal of the dilation tube 32 as indicated with dot-dash lines in FIG. 13.

During air or water supply, the terminal of the dilation tube 32 is not linked with the joint 80.

When air supply is performed to jet air through the nozzle 29 shown in FIG. 2, the electromagnetic valve 73 is opened to feed air drawn with the air pump 71 to the air/water supply channel 27. When water supply is performed to jet water through the nozzle 29, the electromagnetic valve 76 is opened to feed air drawn with the air pump 71 to the water tank 75. When the air in the water tank 75 is thus compressed, the water in the water tank 75 flows into the air/water supply channel 27.

When neither air nor water is supplied, the electromagnetic valves 73 and 76 are closed and the electromagnetic valve 78 is opened. This causes the air drawn with the air pump 71 to leak out through the leakage pipe 79 and join the outside air.

On the other hand, when the air pump 71 is used as a cover dilator, as indicated with dot-dash lines, the terminal of the dilation tube 32 is linked with the joint 80 and the electromagnetic valve 78 is opened. This causes the air drawn with the air pump 71 to flow into the endoscope insertion channel 34 via the dilation tube 32. Thus, the air pump 71 serves as a cover dilator. This embodiment, therefore, obviates the cover dilator 6 and enables realization of an endoscope system at low cost. Furthermore, a space for the cover dilator 6 can be saved.

For suction, the electromagnetic valve 84 is opened, and then body fluid or the like is sucked through the forceps exit 30 and stored in the sucked object storage tank 83 via the suction channel 28. When suction is not performed, the electromagnetic valve 84 is closed, while the electromagnetic valve 85 is opened.

According to this embodiment, merely by inserting the dilation tube cap 33 into the attachment port 59 of the cover holding instrument 58, the insertional part cover 11A can be held and air can be fed to the endoscope insertion channel 34 (the function of a cover dilator becomes available). Consequently, sheathing and other work can be achieved efficiently.

Figure 14:
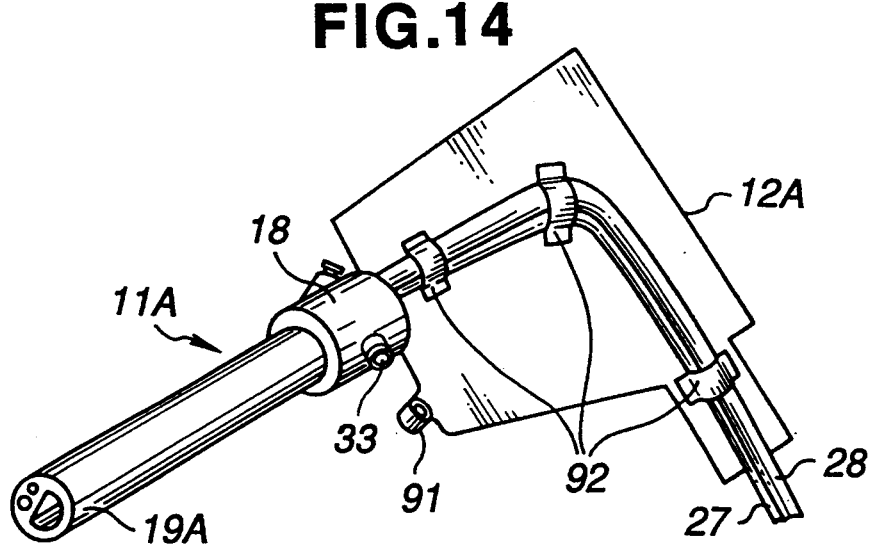
FIG. 14 is an oblique view of an operational part cover according to a fifth embodiment of the present invention.

FIG. 14 shows a major portion of the fifth embodiment of the present invention. In this embodiment, an operational part cover 12A is provided with a dilation tube cap cover 91. The operational part cover 12A and dilation tube cap cover 91 are formed as a unit. The operational part cover 12A has clamps 92 for clamping an air/water supply channel 27 and a suction channel 28 which are projecting from an insertional part cover 11A.

The clamps 92 are made of adhesive tape, which attach the air/water supply channel 27 and suction channel 28 to the operational part cover 12A. The other components are identical to those in the first embodiment.

In this embodiment, after the insertional part of a coverable endoscope 2B is inserted into the insertional part cover 11A and thus sheathed with the insertional part cover 11A, the operational part cover 12A which is independent of the insertional part cover 11A is used to wrap an operational part 12B of the coverable endoscope 2B. At the same time, the dilation tube cap cover 91 is attached to the dilation tube cap 33. Thus, the endoscope system gets ready for endoscopic examination.

According to this embodiment, the dilation tube cap 33 is shielded with the dilation tube cap cover 91, and, therefore, protected from contamination via a hand or fingers. Since the air/water supply channel 27 and suction channel 28 are fixed to the operational part cover 12A, the air/water supply channel 27 and suction channel 28 will not move around within the operational part cover 12A. Furthermore, when the coverable endoscope 2B is gripped with the operational part cover 12A attached, the air/water supply channel 27 and suction channel 28 can be stationed at a position not interfering with the grip.

As described above, according to the first to fifth embodiments, since a cover member is included to shield a dilation tube cap, the dilation tube cap can be protected reliably from being touched with a hand or fingers during surgical operation. Eventually, spread of contamination throughout the cover attributable to the fact that the dilation tube cap is contaminated can be reliably prevented.

Figure 15:
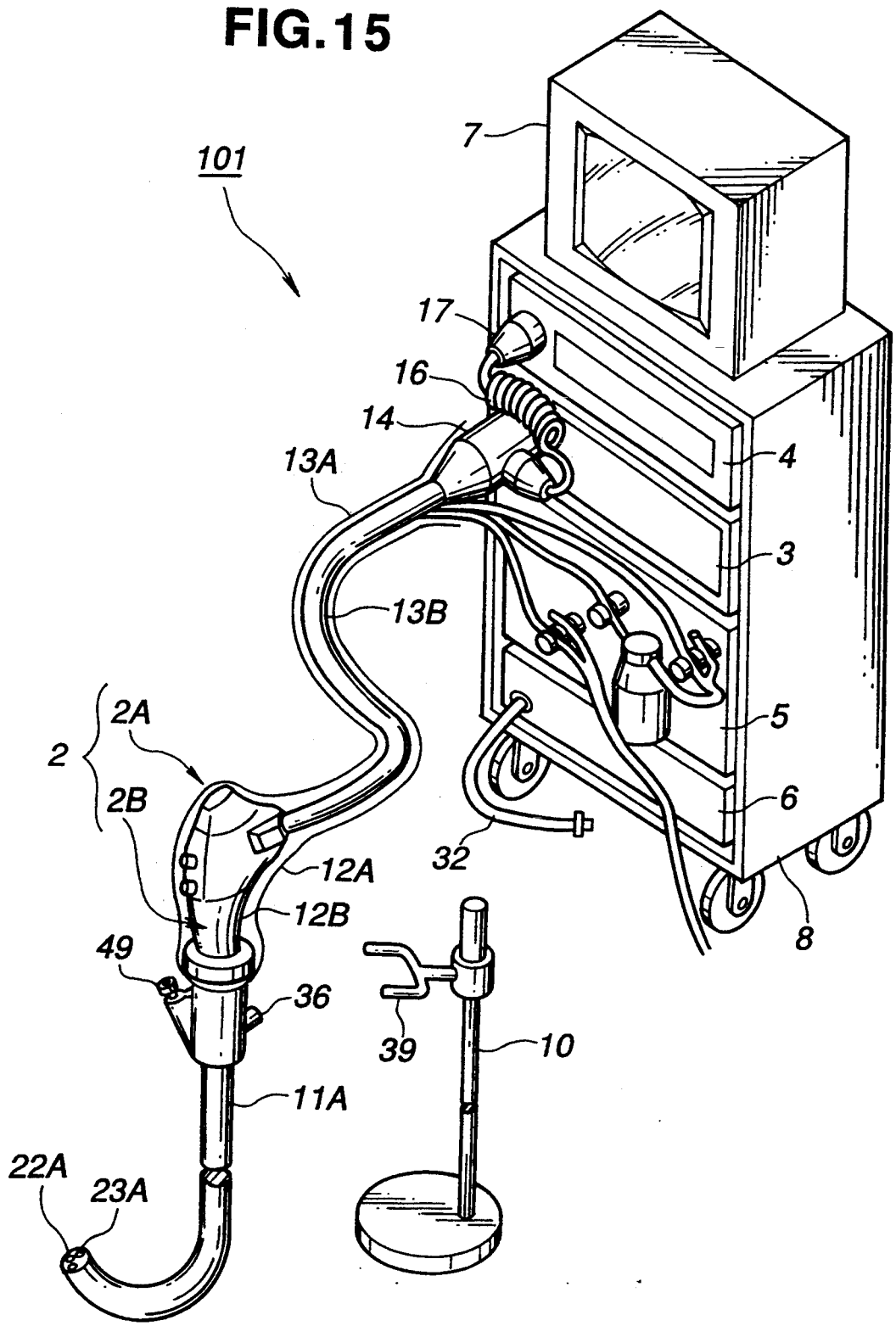
FIGS. 15 to 19 relate to a sixth embodiment of the present invention.

FIG. 15 shows a covered endoscope system 101 according to the sixth embodiment of the present invention. In the covered endoscope system 101, a cover dilator 6 has not only the function of the first embodiment but also a hole boring detecting function. Components identical to those in the first embodiment bear the same numerals.

Figure 16:
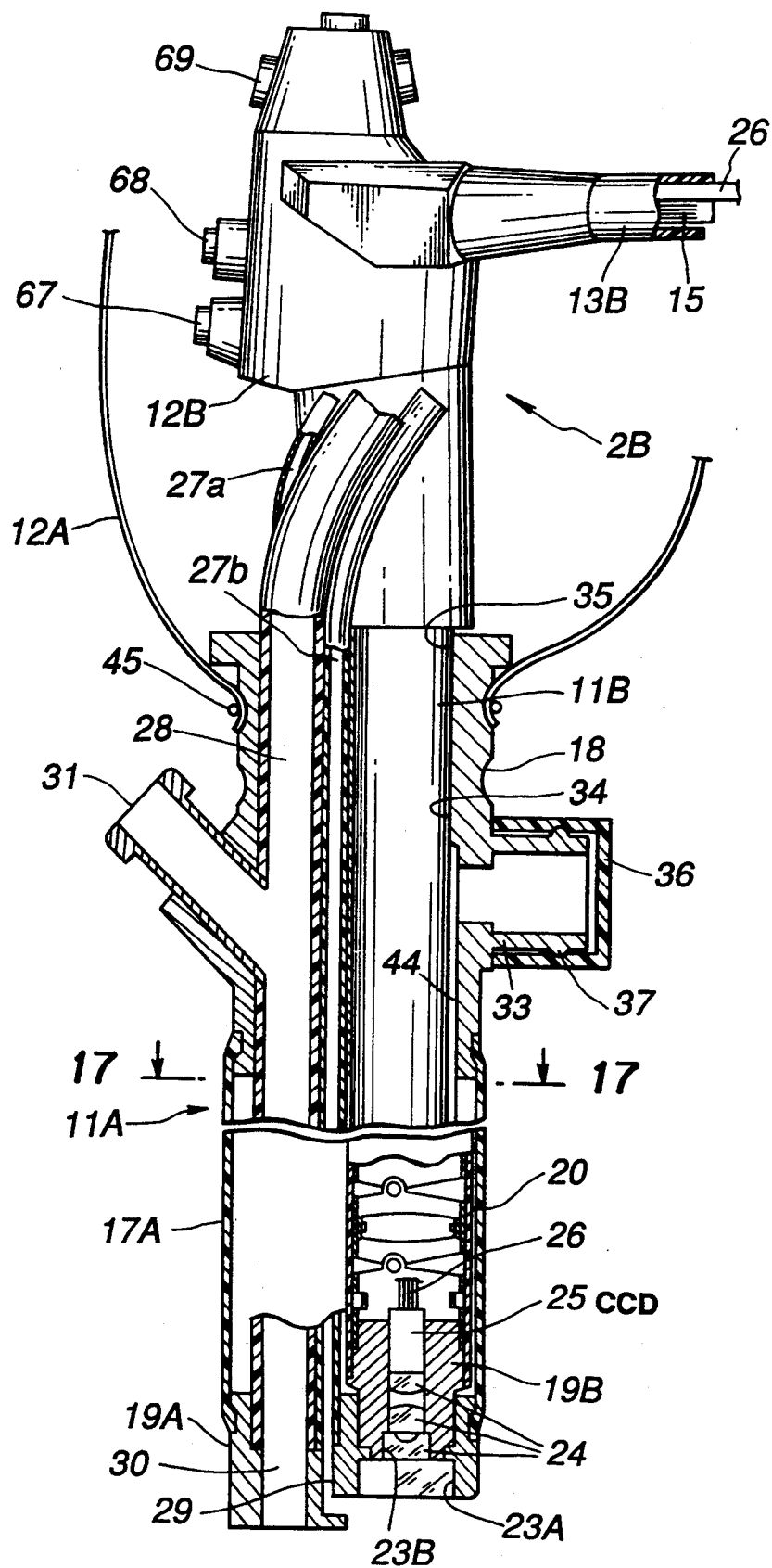
Figure 17:
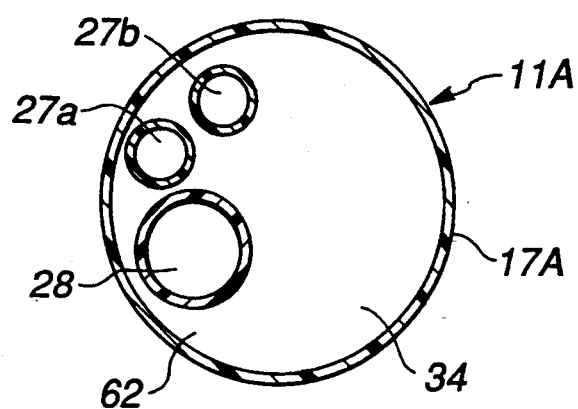

FIG. 16 shows a covered endoscope 2 of the fifth embodiment for use in the endoscope system 101. In the covered endoscope 2 of this embodiment, as shown in FIG. 17, an insertional part cover 11A has an air supply channel 27a, a water supply channel 27b, and a suction channel 28. The remaining portion of an insertional part cover skin 17A excluding the above channels is an endoscope insertion channel 34.

That is to say, the air/water supply channel 27 in the first embodiment is provided as the air supply channel 27a and water supply channel 27b independently in this embodiment. The air supply channel 27a and water supply channel 27b merge at their terminals and open onto the common nozzle 29. The proximal ends of the air supply channel 27a and water supply channel 27b are linked with the fluid control apparatus 5 as shown in FIG. 15.

Figure 18:
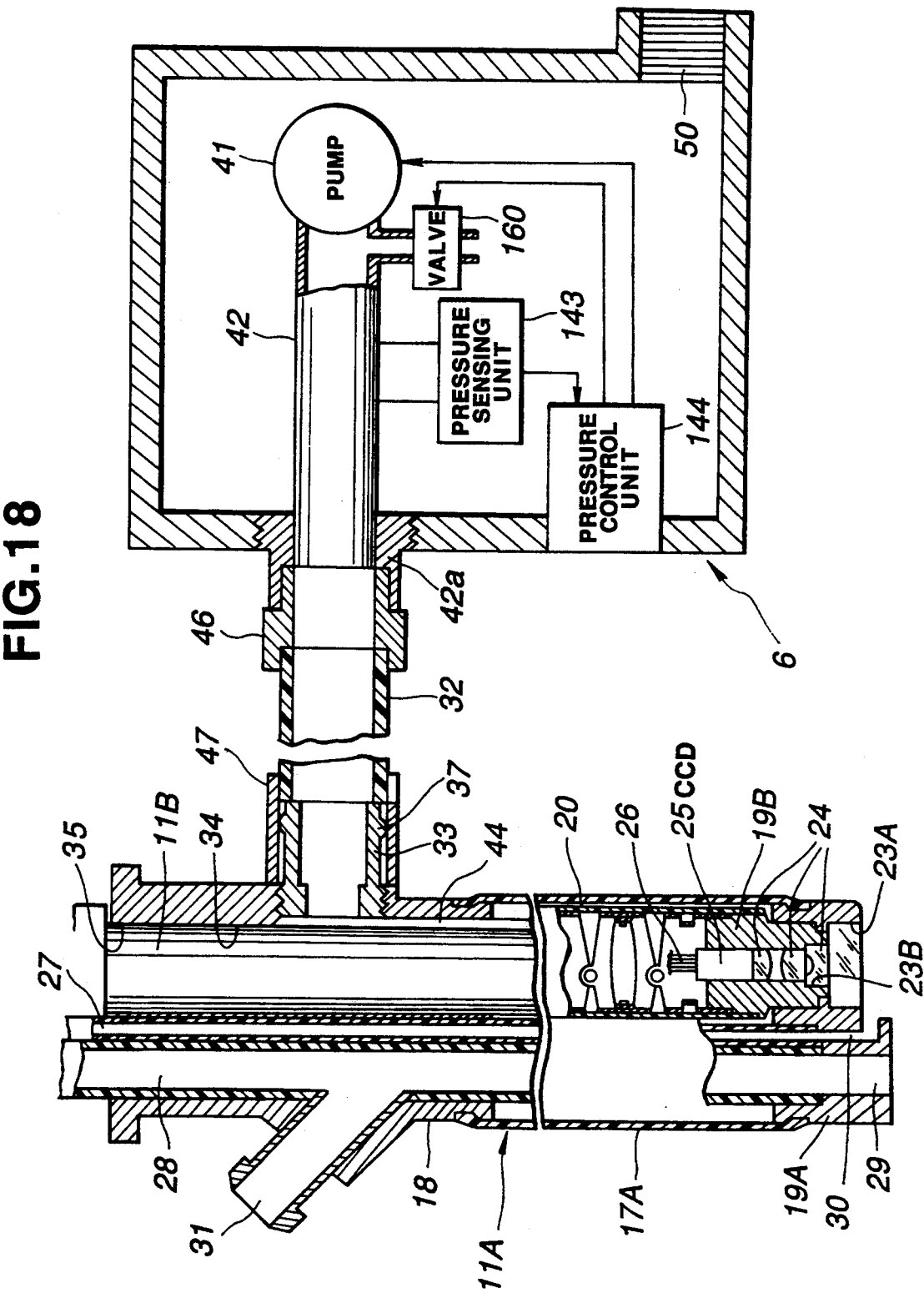

FIG. 18 shows a composition of a cover dilator 6 having a hole boring sensing function. In this embodiment, once an insertional part 11B of a coverable endoscope 2B is sheathed with an insertional part cover 11A, hole boring sensing can be done easily with a dilation tube 32 coupled where "hole boring" refers to the creation of a small pin-hole in the endoscope cover.

The cover dilator 6 is composed of an air pump 41, an air pipe 42, a pressure sensing unit 143, and a pressure control unit 144.

The proximal end of the air pipe 42 is linked with the air pump 41, and the terminal thereof is provided with a base 42a and linked with the proximal end of the dilation tube 32. Air drawn with the air pump 41 is supplied to the dilation tube 32 via the air pipe 42.

The air pipe 42 is branched in the middle thereof and linked with the pressure sensing unit 143. The pressure sensing unit 143 senses the pressure in the air pipe 42. The air pipe 42 opens onto the outside via an electromagnetic valve 160. The opening or closing of the electromagnetic valve 160 is controlled by the pressure control unit 144.

The pressure control unit 144 is connected to the air pump 41 and to the pressure sensing unit 143, and controls the air supply operation of the air pump 41 according to an external operation or a signal sent from the pressure sensing unit 143.

When the function of the cover dilator 6 is unused, as shown in FIG. 15, the terminal of the dilation tube 32 is uncoupled with the dilation tube cap 33 but opens onto the outside air so as to evacuate air drawn with the air pump 41 to the outside.

Figure 19:
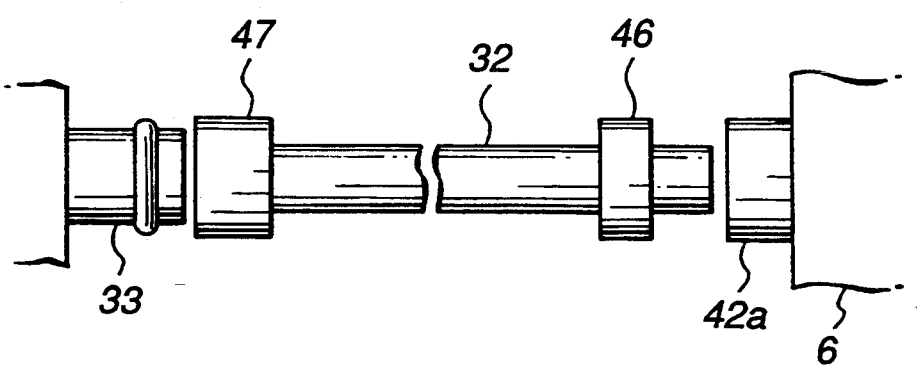

As shown in FIG. 19, one end of the dilation tube 32 is provided with a cap 46 that can be attached to or detached from a base 42a mounted on the end of the air pipe 42 of the cover dilator 6. The other end thereof is provided with a cap 47 that can be attached to or detached from the dilation tube cap 33. The caps 46 and 47 may be one-touch joints or volute joints (connectors).

Since the caps 46 and 47 are mounted on both ends of the dilation tube 32 and can be attached or detached easily, the dilation tube 32 can be replaced effortlessly. For example, two dilation tubes 32 are prepared, and one of them is used as a sheathing dilation tube. Thereafter, the dilation tube is removed and the other tube is mounted. Thus, the other tube can be used as an unsheathing dilation tube.

Furthermore, since the dilation tube 32 can be removed, the dilation tube 32 can be disinfected.

When a coverable endoscope 2B is sheathed with an insertional part cover 11A, as shown in FIG. 18, the terminal of the dilation tube 32 is airtightly coupled with the dilation tube cap 33. Then, air drawn with the air pump 41 is fed to an endoscope insertion channel 34 via the dilation tube cap 33, and thus dilates the endoscope insertion channel 34. This makes it easy to insert the insertional part 11B.

Next, the operation of the sixth embodiment will be described.

When the coverable endoscope 2B is inserted into (sheathed with) the insertional part cover 11A of the cover 2, as shown in FIG. 15, a semi-circular holder 39 of a cover holding instrument 10 is used to hold a flange formed at the upper end of an insertional part locking cap 18.

Then, when the terminal of the dilation tube 32 is coupled with the dilation tube cap 33, air is fed from the cover dilator 6 to the endoscope insertion channel 34. The air leaks out from an opening 35 to the outside.

When the coverable endoscope 2B is inserted through the opening 35, the opening 35 is almost blocked. Air passes through a notch 44 and dilates an insertional part cover skin 17A. The insertional part 11B can, therefore, be inserted smoothly. The front surface of a distal end 19B can be brought into contact with the inner surface of a cover distal end 19. Thus, the coverable endoscope 2B is sheathed.

When hole boring sensing is to be performed on the insertional part cover 11A (with the dilation tube 32 coupled with the dilation tube cap 33), the pressure control unit 43 is operated to control an air supply pressure. The control causes the air supply pressure to drop. Air will, therefore, not leak out from a gap between the opening 35 and coverable endoscope 2B.

When the pressure in the endoscope insertion channel 34, that is, the pressure in the air pipe 42 has reached a certain pressure, the pressure sensing unit 143 sends a signal. In response to the signal, the pressure control unit 144 de-energizes the air pump 41. Thereafter, the pressure sensing unit 143 checks the endoscope insertion channel 34; that is, the air pipe 42 for a pressure change, and thus senses hole boring occurring on the insertional part cover 11B. To reduce the air supply pressure, the electromagnetic valve 160 may be opened. Then, when a certain pressure is attained, the electromagnetic valve 160 may be closed in response to a signal sent from the pressure sensing unit 143.

When hole boring sensing confirms that no hole is bored, the terminal of the dilation tube 32 is decoupled from the dilation tube cap 33. Then, an operational part 12B and a universal cord 13B are sheathed with an operational part cover 12A and a universal cord cover 13A respectively. A dilation tube cap cover is attached to the dilation tube cap 33. Thus, the endoscope becomes usable for endoscopic examination.

According to this embodiment, since the cover dilator 6 has a means for sensing hole boring, the cover dilator 6 can sense hole boring by itself. No extra space is needed.

Once the dilation tube 32 is coupled with the dilation tube cap 33, not only the cover 2A can be attached but also hole boring sensing can be performed. The dilation tube need not be replaced, which saves labor and shortens working hours.

An endoscope employed in conjunction with the cover 2A is not limited to the coverable endoscope 2B but may be an endoscope that is used without the cover 2A; that is, used with bare body.

Figure 20:
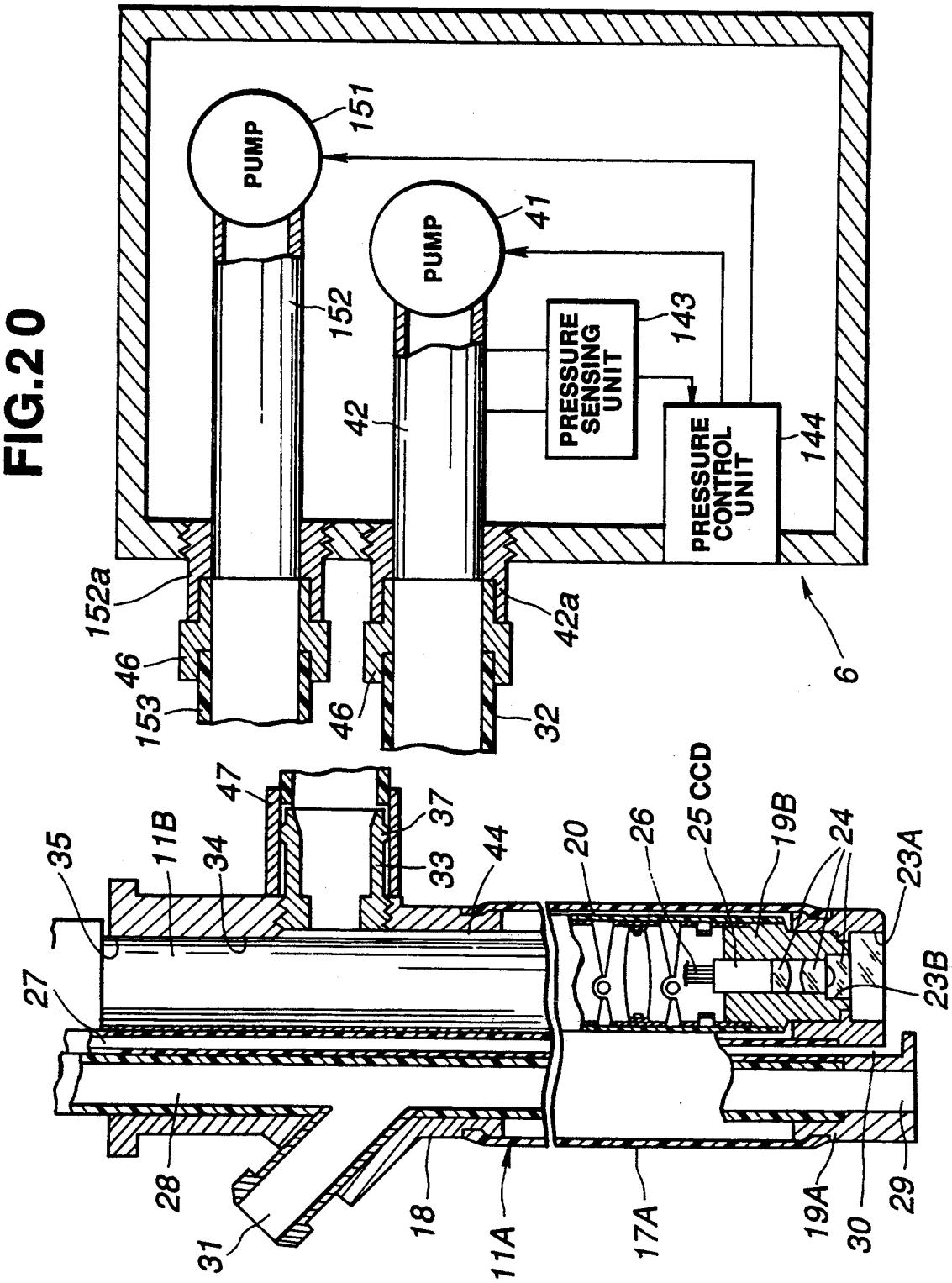
FIG. 20 is a schematic diagram of a composition of a cover dilator according to a seventh embodiment of the present invention.

FIG. 20 shows a major portion of the seventh embodiment of the present invention. In this embodiment, different dilation tubes are used according to whether a coverable endoscope 2B is sheathed with or unsheathed from an insertional part cover 11A. This reliably prevents occurrence of infection or the like.

As shown in FIG. 20, a cover dilator 6 in this embodiment has a second air pump 151 and a second air pipe 152 in addition to the components in the sixth embodiment. The proximal end of the second air pipe 152 is linked with the second air pump 151, and the terminal thereof is provided with a base 152a with which a second dilation tube 153 is coupled. Air drawn with the second air pump 151 is supplied to the second dilation tube 153 via the air pipe 152. The ends of the dilation tube 153 are provided with caps 46 and 47, similarly to those in the sixth embodiment.

The second air pump 151 is connected to a pressure control unit 144. The air supply operation of the second air pump 151 is controlled by a pressure control unit 144.

In this embodiment, the dilation tube 32 to be linked with an air pipe 42 is, for example, used for sheathing and hole boring sensing. The second dilation tube 153 to be linked with the second air pipe 152 is used for unsheathing. The dilation tube 32 used for sheathing must have been fully disinfected.

The dilation tube 32 used for sheathing and the dilation tube 153 used for unsheathing have different colors or bear different ID marks so as to be differentiated from each other.

When the coverable endoscope 2B is sheathed with the insertional part cover 11B or hole boring sensing is performed, the sheathing dilation tube 32 is coupled with a dilation tube cap 33. Then, the pressure control unit 144 is operated to actuate the air pump 41. When the coverable endoscope 2B is unsheathed from the insertional part cover 11B, the unsheathing dilation tube 153 is coupled with the dilation tube cap 33. Then, the pressure control unit 144 is operated to actuate the air pump 151. In this embodiment, the dilation tube cap 33 need not be covered for endoscopic examination.

When the dilation tube cap 33 is not covered for endoscopic examination, if a single dilation tube 32 is used to sheath or unsheath the coverable endoscope 2B with or from the insertional part cover 11B, the following problem arises: when the coverable endoscope 2B is unsheathed from the insertional part cover 11B, since the covered endoscope 2 has been used, the endoscope 2 is contaminated with body fluid or the like.

It is, therefore, conceivable that the dilation tube cap 33 is also contaminated. Then the dilation tube 32 to be coupled with the dilation tube cap 33 will also be contaminated. If the contaminated dilation tube 32 is used to sheath the coverable endoscope 2B with a new insertional part cover 11A, the insertional part cover 11A that must be clean is contaminated by the contaminated dilation tube.

In this embodiment, since the sheathing dilation tube 32 and the unsheathing dilation tube 153 are available, the sheathing dilation tube 32 can be kept clean all the time. Consequently, when the coverable endoscope 2B is sheathed with the insertional part cover 11A, the insertional part cover 11A can be prevented from being contaminated via the dilation tube 32.

Figure 21:
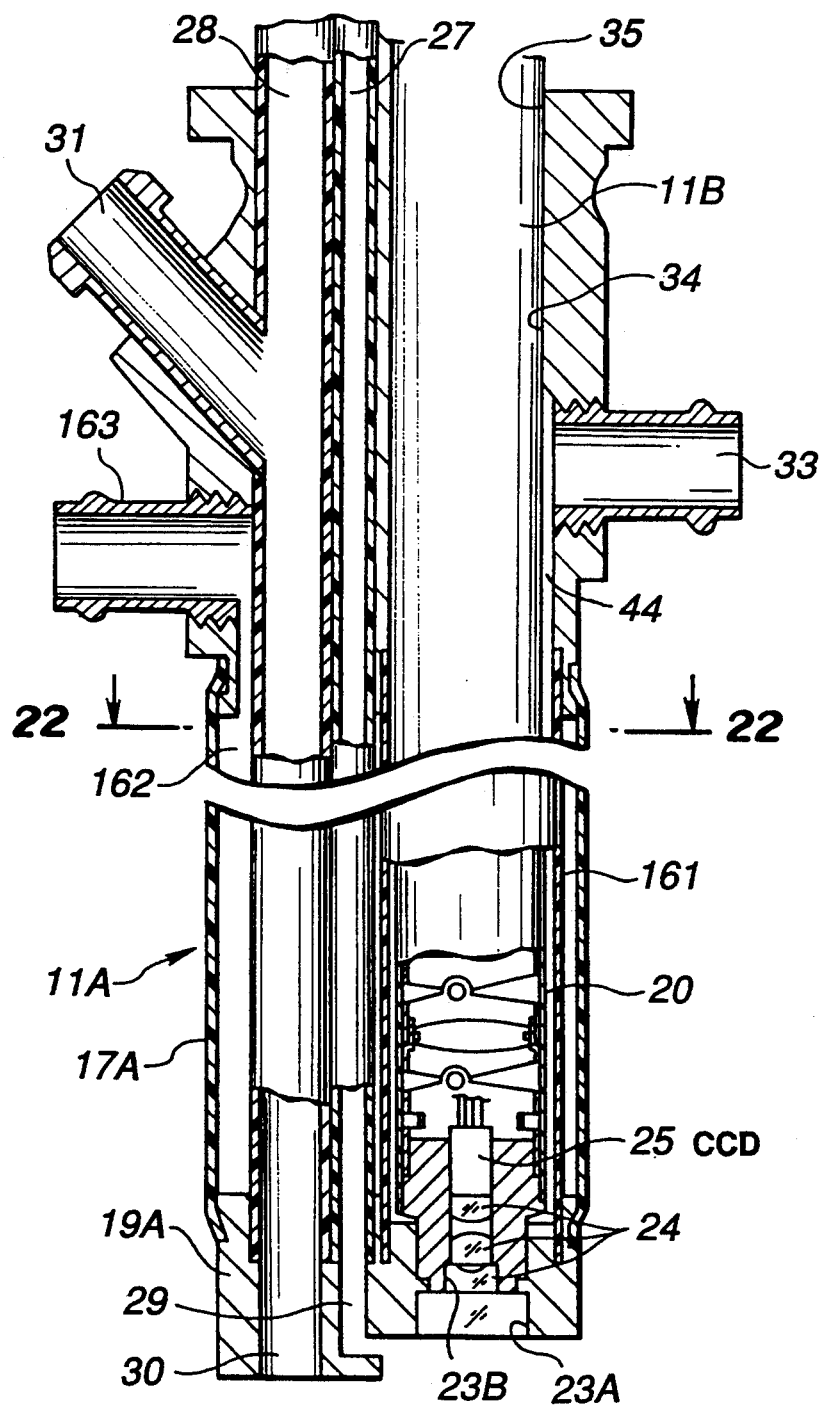
FIGS. 21 and 22 relate to an eighth embodiment of the present invention.

FIG. 21 shows a major portion of the eighth embodiment of the present invention. This embodiment enables hole boring sensing for not only an endoscope insertion channel 34 but also for other tubes.

Figure 22:
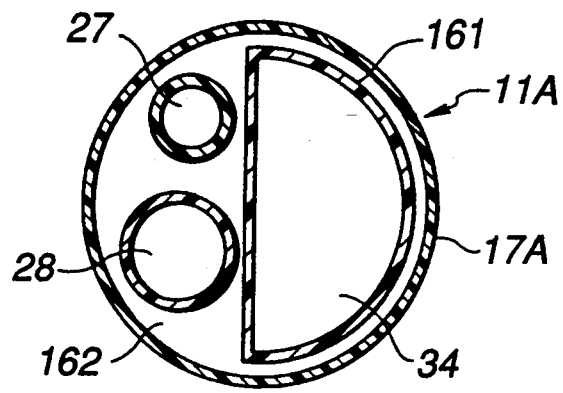

The insertional part cover 11A shown in FIGS. 21 and 22 is identical to the insertional part cover 11A shown in FIG. 16 except that an endoscope insertion channel tube 161 is incorporated in an insertional part cover skin 17A. The channel tube 161 is made of, for example, a soft resin.

The upper end of the channel tube 161 is fixed airtightly to the lower end of an operational part locking cap 18, and communicates with an opening 35 and with a dilation tube cap 33.

The lower end of the endoscope insertion channel tube 161 is fixed airtightly to a cover distal end 19A having a cover observation window 23A. Similarly to the sixth embodiment, when air is supplied through the dilation tube cap 33, the endoscope insertion channel tube 161 dilates to enable sheathing or unsheathing of an insertional part 11B.

When a coverable endoscope 2B is inserted into the endoscope insertion channel tube 161, the coverable endoscope 2B can be inserted into the insertional part cover 11A without being caught by an air/water supply channel 27 or a suction channel 28, and thus sheathed with the insertional part cover 11A.

Due to the incorporation of the endoscope insertion channel tube 161, the insertional part cover 11A has a cross section shown in FIG. 22. That is to say, the endoscope insertion channel tube 161 forming an endoscope insertion channel 34 into which the insertional part 11B is inserted, and an air/water supply tube and a suction tube forming the air/water supply channel 27 and suction channel 28 respectively are arranged in an internal space 162 of the insertional part cover skin 17A.

The internal space 162 is the portion of a space surrounded with the cover distal end 19A, insertional part cover skin 17A, and operational part locking cap 18 excluding the air/water supply channel 27 and endoscope insertion channel tube 161.

In this embodiment, the operational part locking cap 18 is provided with a ventilation cap 163 that communicates with the internal space 162 and with which a dilation tube 32 can be coupled. When the dilation tube 32 is coupled with the ventilation cap 163, hole boring occurring on the insertional part cover 11A can be sensed. Next, the operation will be described.

When a coverable endoscope 2B is sheathed width the insertional part cover 11A, the terminal of the dilation tube 32 is coupled with the dilation tube cap 33. Then, while the endoscope insertion channel tube 161 is being dilated, the coverable endoscope 2B is inserted into and sheathed with the insertional part cover 11A.

When hole boring on the insertional part cover 11A is to be sensed, the dilation tube 32 is coupled with the ventilation cap 163. Then, the insertional part cover skin 17A is pressurized internally, which enables hole boring sensing.

In the aforesaid prior art, it is only the dilation tube cap 33 with which the dilation tube 32 is coupled. When the insertional part cover 11A has the endoscope insertion channel tube 161, therefore, only the endoscope insertion channel tube 161 can be pressurized. This means that the insertional part cover skin 17A cannot be pressurized.

In this embodiment, since the ventilation cap 163 is created, the insertional part cover skin 17A can be pressurized to enable hole boring sensing.

Figure 23:
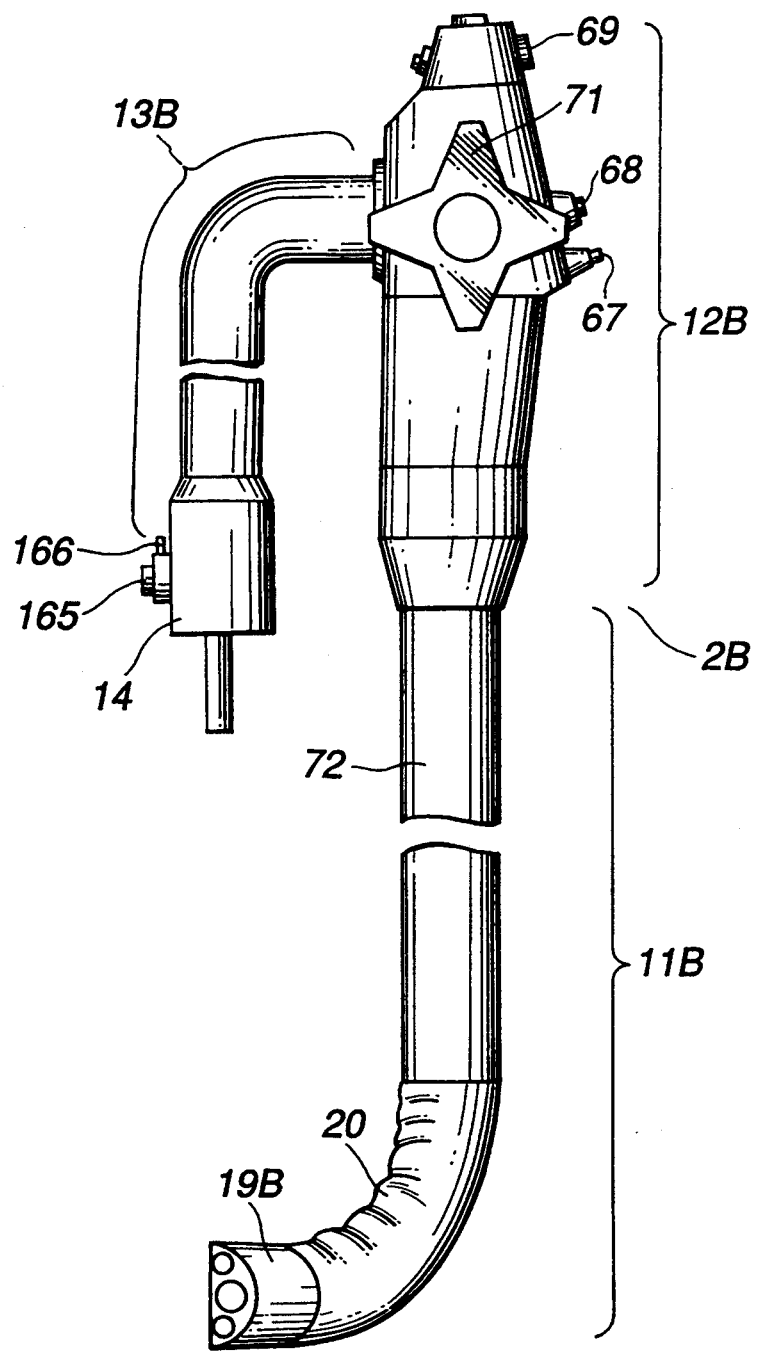

FIG. 23 shows a coverable endoscope 2B in the ninth embodiment of the present invention. This embodiment permits hole boring sensing for a coverable endoscope 2B. In the coverable endoscope shown in FIG. 23, a connector 14 for a universal cord 13B has a cable joint 165 which is linked with a cable 16. The cable joint 165 has a securing pin 166. The inner portion of the cable joint 165 joins the inside of the coverable endoscope 2B, and has a contact pin which is not shown.

As described in conjunction with FIG. 3, an operational part 12B has an air/water supply switch 67, a suction switch 68, and an image select switch 69 for selecting, for example, a still imaging mode. A curvature knob 71 is installed so as to be detachable.

An insertional part 11B is made up of a flexible portion 72 that is flexible and elongated, a bending section 20 formed at the distal end of the flexible portion 72, and a distal end 19B formed at the distal end of the bending section 20. The bending section 20 can be bent by operating the curvature knob 71.

Figure 24:
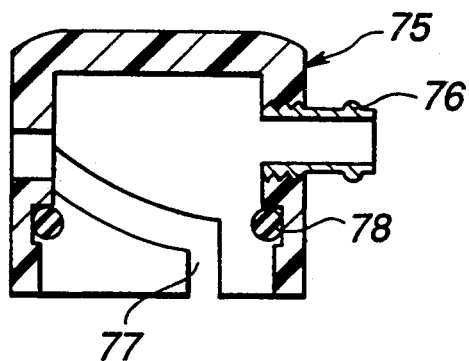
FIGS. 23 to 25 relate to a ninth embodiment of the present invention.

FIG. 24 shows a cross section of a waterproof cap 75 attached airtightly to the cable joint 165. The waterproof cap 75 is made of a hard resin, having a ventilation base 76 with which a dilation tube 32 is linked, a cam groove 77 that engages with the securing pin 166 of the cable joint 165, and an elastic ring 78 for holding the cable joint 165 airtightly.

Figure 25:
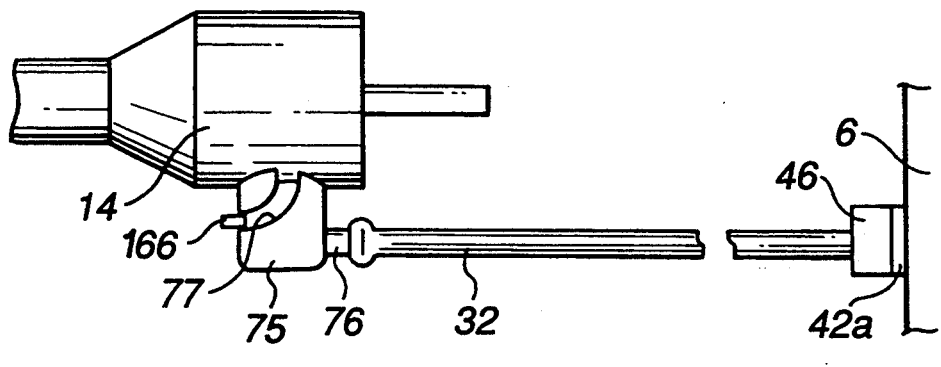

FIG. 25 shows a state that the waterproof cap 75 is attached to the cable joint 165 and the dilation tube 32 is coupled with the ventilation base 76. The proximal end of the dilation tube 32 is connected to a cover dilator 6, and the waterproof cap 75 is fixed to the cable joint 165 with the securing pin 166.

In this embodiment, air drawn with the cover dilator 6 passes through the ventilation base 76, flows into a coverable endoscope 2B via the cable joint 165, and then pressurizes the coverable endoscope 2B internally.

According to this embodiment, the cover dilator 6 can sense hole boring occurring in the coverable endoscope 2B.

In the aforesaid sixth to ninth embodiments, a forceps insertion port and a dilation tube cap are separated from each other by an angle 90° or larger. The aforesaid embodiments can be combined in any other manner to form different embodiments.

As described so far, according to the sixth to ninth embodiments, a cover dilator has a means for sensing hole boring. The cover dilator alone enables sheathing or unsheathing of a coverable endoscope and hole boring sensing. This saves space.

Figure 26:
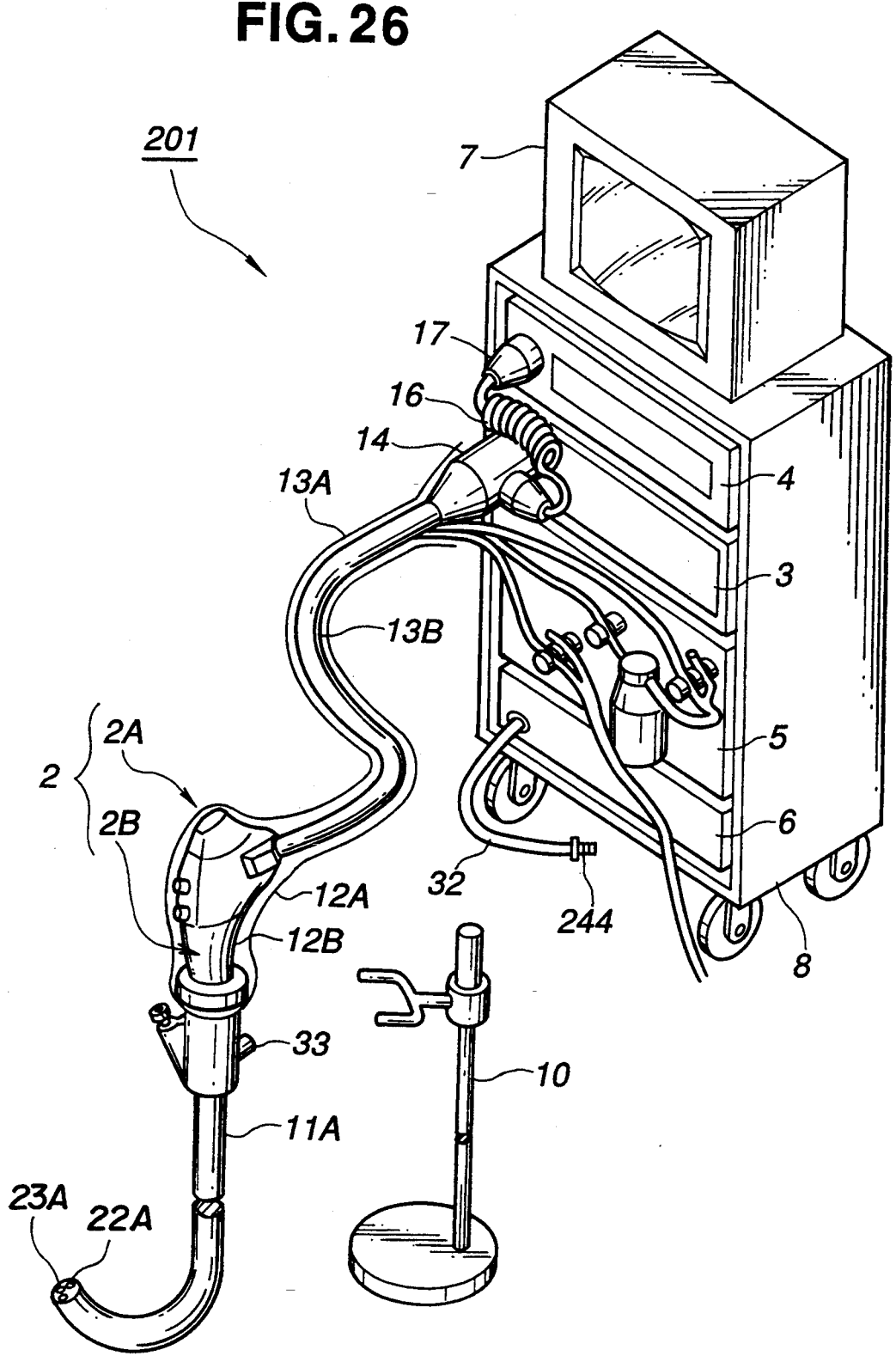
FIGS. 26 to 28 relate to a tenth embodiment of the present invention.

FIG. 26 shows a configuration of a covered endoscope system 201 having the tenth embodiment of the present invention.

Figure 28:
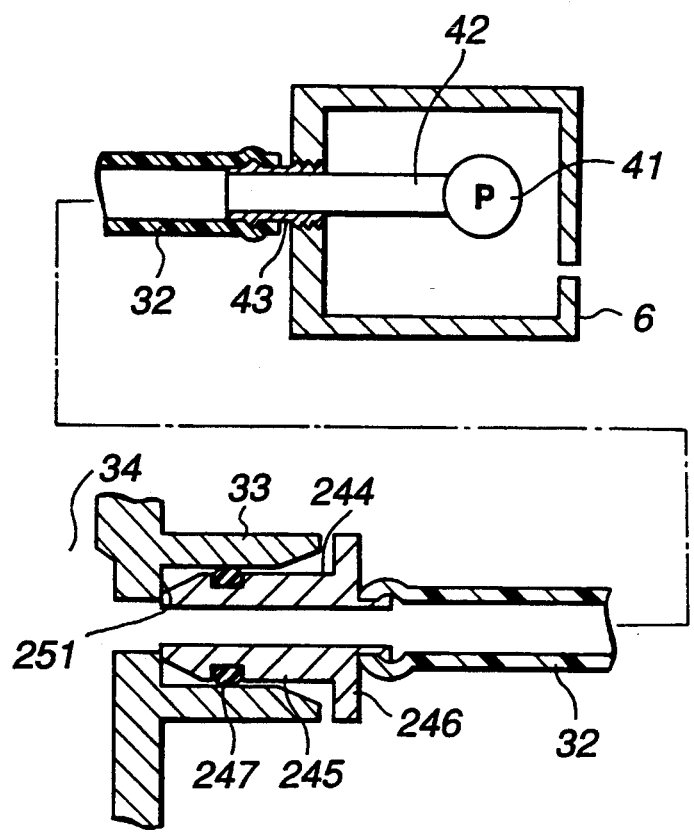

The system 201 shown in FIG. 26 is identical to the system 1 shown in FIG. 1 except that the terminal of a dilation tube 32 is provided with a connection cap 244 which is enlarged in FIG. 28. Components identical to those shown in FIG. 1 bear the same numerals.

Figure 27:
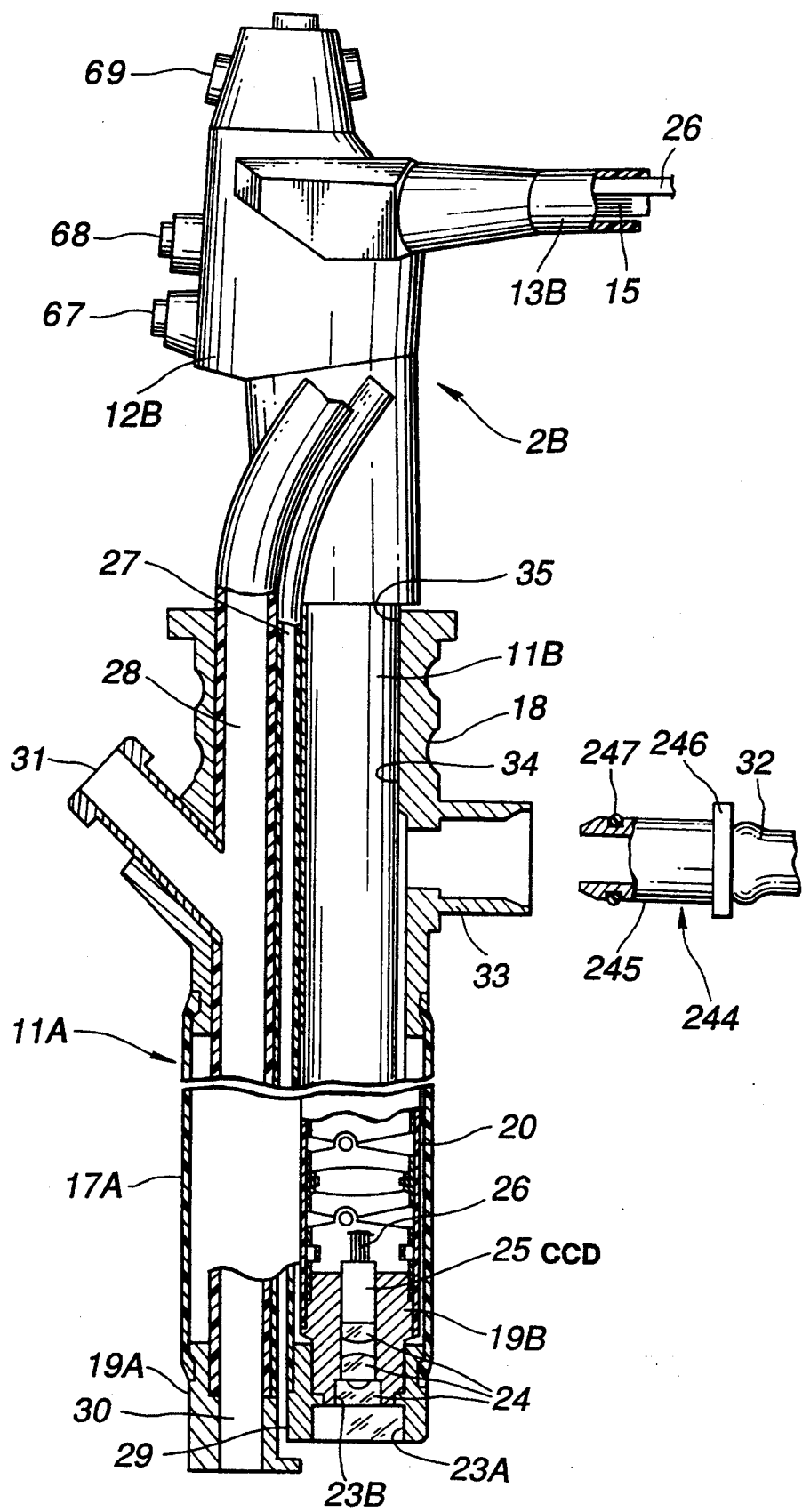

A cover 2A in this embodiment has a dilation tube cap 33 into which the connection cap 244 is fitted as shown in FIGS. 27 and 28.

Then, when an insertional part 11B of a coverable endoscope 2B is inserted into or removed from an insertional cover 11A, as shown in FIG. 27, the connection cap 244 at the terminal of the dilation tube 32 is coupled with a dilation tube cap 33. Then, air is supplied to an endoscope insertion channel 34 via the dilation tube cap 33, and thus dilates the endoscope insertion channel 34. This permits easy insertion or removal of the insertional part 11B.

The connection cap 244 includes a ring type joint 245 that is fitted into the dilation tube cap 33 and a flange 246 formed at the proximal end of the joint 245. The terminal of the dilation tube 32 is coupled with the projection behind the flange 246.

The inner diameter of the dilation tube cap 33 is slightly larger than the outer diameter of the joint 245 of the connection cap 244, so that the joint 245 can be fitted into the dilation tube cap 33.

A groove is dug in the outer circumferential surface of the joint 245 and an elastic ring 247 is embedded in the groove, which ensures airtightness between the dilation tube cap 33 and joint 245 which are to be coupled with each other.

The joint 245 is formed longer than the dilation tube cap 33, so that the flange 246 of the connection cap 244 will not touch the open end of the dilation tube cap 33. Specifically, as shown in FIG. 28, a step 251 projecting inward is formed on the proximal inner circumferential surface of the dilation tube cap 33. Even when the distal end of the joint 245 which is fitted into the dilation tube cap 33 is inserted to a position in contact with the step 251, the flange 246 is positioned apart from the open end of the dilation tube cap 33.

When a hand or the like touches the end or outer circumferential surface of the dilation tube cap 33 during endoscopic examination, the portion touched by the hand or the like may be contaminated. Nevertheless, when the joint 245 of the connection cap 244 attached to the terminal of the dilation tube 32 is fitted into the dilation tube cap 33 in order to unsheath the coverable endoscope 2B, the portion of the joint 245 in contact with the dilation tube cap 33 remains uncontaminated.

Next, the operation of this embodiment will be described. After examination is completed, the joint 245 of the connection cap 244 of the dilation tube 32 is fitted into the dilation tube cap 33 in order to unsheath the coverable endoscope 2B. In this case, the portion of the dilation tube cap 33 in contact with the dilation tube 32, that is, the portion of the dilation tube cap 33 in contact with the joint 245 is only the inside of the dilation tube cap 33 which has not been contaminated. The connection, therefore, will not contaminate the dilation tube 32.

In the aforesaid prior art, the foregoing means is not included. Therefore, when the terminal of the dilation tube 32 is coupled with the dilation tube cap 33, there is a possibility that contamination is spread. In this embodiment, the spread of contamination can be prevented. Eventually, occurrence of infection can be reliably prevented.

An endoscope used in conjunction with the cover 2A is not limited to the coverable endoscope 2B but may be an endoscope which is used without the cover 2A; that is, used with bare body.

Figure 29:
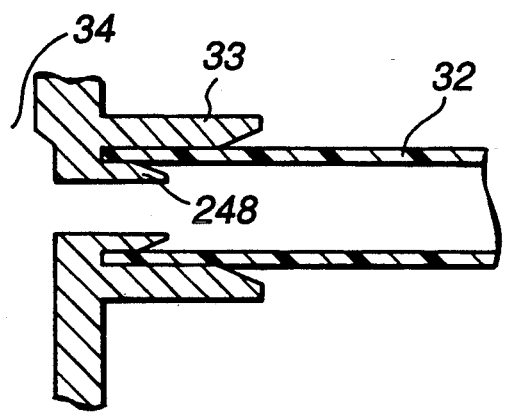
FIG. 29 is a cross-sectional view of a joint of a dilation tube coupled with a dilation tube cap according to an eleventh embodiment of the present invention.

FIG. 29 shows a mechanism for coupling a dilation tube cap 33 with a dilation tube 32 in the eleventh embodiment of the present invention. In this embodiment, a ring type projection 248 whose outer diameter is equal to or slightly larger than the inner diameter of the dilation tube 32 is formed on the inner surface of the dilation tube cap 33. The inner diameter of the dilation tube cap 33 is larger than the outer diameter of the dilation tube 32.

When the terminal of the dilation tube 32 is inserted into a gap between the outer surface of the ring type projection 248 and the inner surface of the dilation tube cap 33, the terminal of the dilation tube 32 can be airtightly coupled with the dilation tube cap 33.

According to this embodiment, the dilation tube 32 has almost the same function as that in the tenth embodiment and obviates the connection cap 244 in the tenth embodiment, which, therefore, can be provided at low cost.

In the tenth and eleventh embodiments, an endoscope used in conjunction with the cover 2A is not limited to the coverable endoscope 2B but may be an endoscope which is used without the cover 2A; that is, used with the bare body.

The aforesaid embodiments may be combined in any other manner to form different embodiments. For example, in the aforesaid embodiments, the forceps insertion port and dilation tube cap may be separated from each other by an angle of 90° or larger.

As described so far, according to the tenth and eleventh embodiments, the portion of the dilation tube cap in contact with the dilation tube is the inside of the dilation tube cap. The contact portion can be prevented effectively from being touched with a glove or the like. This leads to prevention of spread of contamination via the dilation tube cap.

Figure 30:
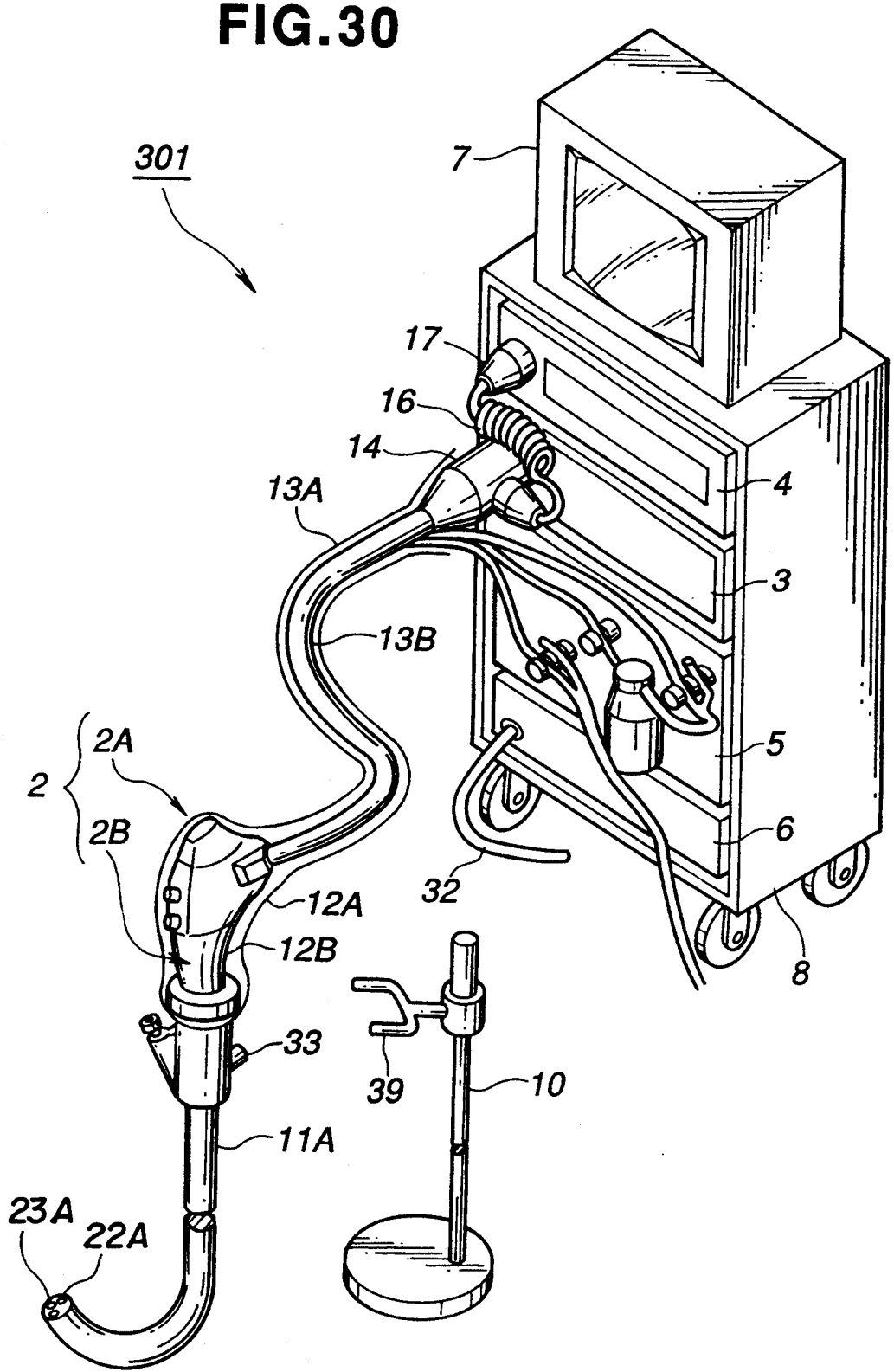
FIGS. 30 to 31 relate to a twelfth embodiment of the present invention.
Figure 31:
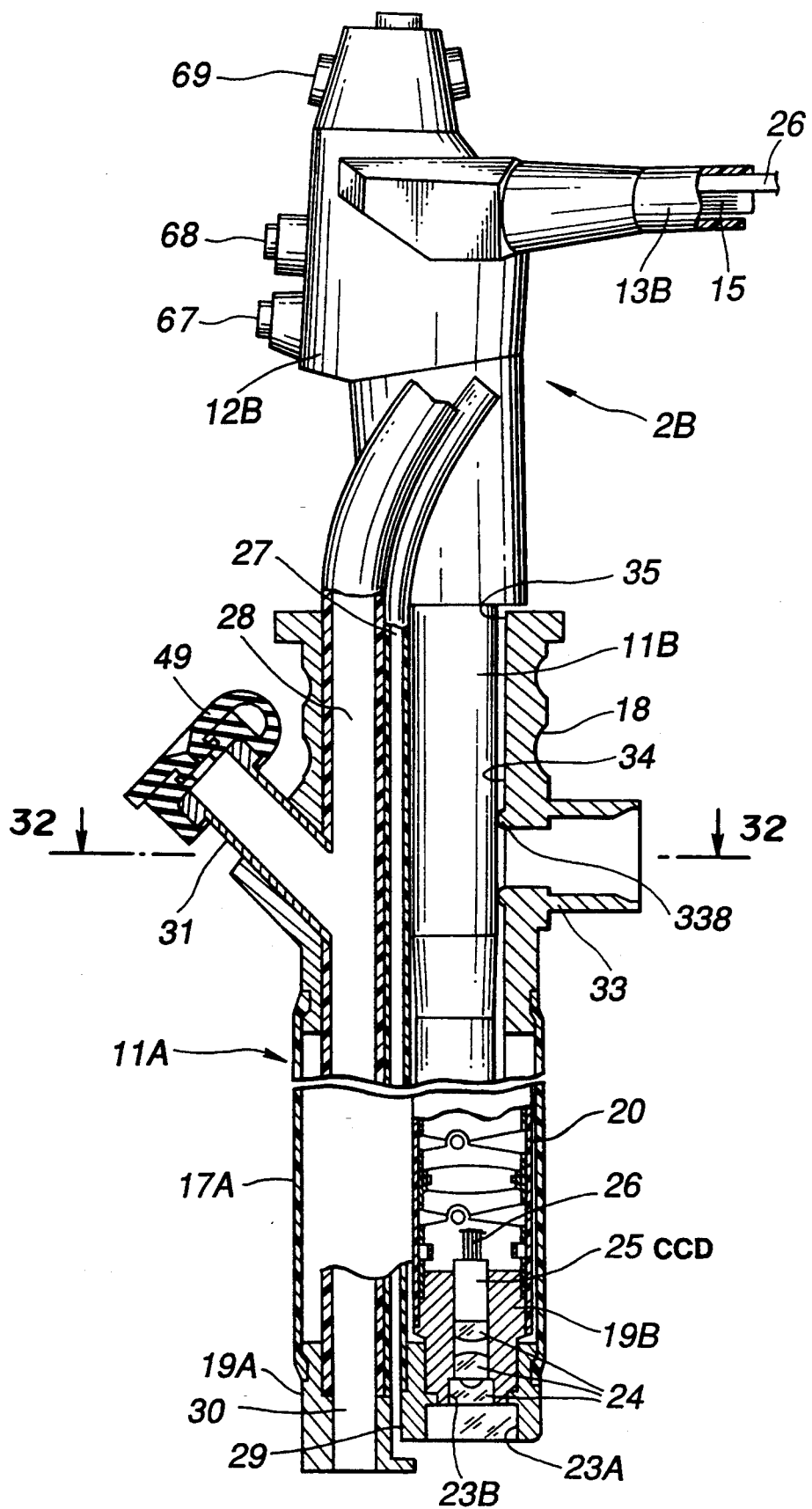

A covered endoscope system 301 shown in FIG. 30 has a covered endoscope in the twelfth embodiment of the present invention shown in FIG. 31.

A covered endoscope 2 shown in FIG. 31 is identical to the covered endoscope 2 shown in FIG. 2 except that a proximal opening of a dilation tube cap 33 communicating with an endoscope insertion channel 34 has a projection 338 projecting toward the endoscope insertion channel 34.

Figure 33:
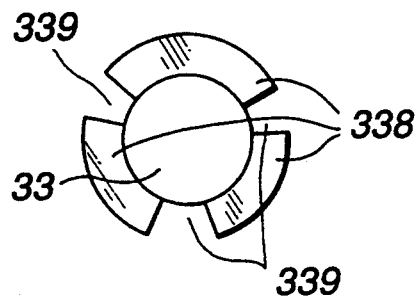
FIG. 33 is a front view of a projection formed on a dilation tube cap, viewing the projection from an endoscope insertion channel.

The projection 338 is shaped like a ring as shown in FIG. 33. The ring type projection 338 has notches 339, whereby when an insertional part 11B is inserted into the endoscope insertion channel 34, the proximal opening of the dilation tube cap 33 will not be blocked with the insertional part 11B. Air fed through the dilation tube cap 33 can, therefore, be fed to the endoscope insertion channel 34 via the notches 339.

Figure 32:
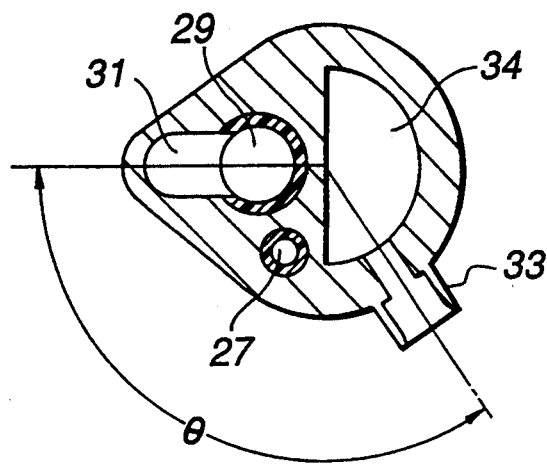
FIG. 32 shows an 32—32 cross section of FIG. 31 and a cross section of an insertional part cover.

As shown in FIG. 32, a forceps insertion port 31 and the dilation tube cap 33 are separated from each other by an angle $\theta$ that is larger than 90°.

Figure 34:
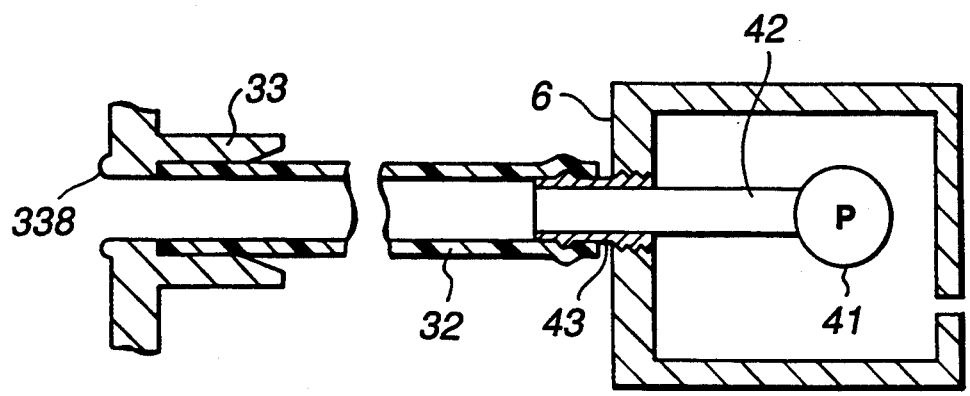
FIG. 34 shows a cover dilator and a dilation tube cap connected to each other via a dilation tube.

When the insertional part 11B of coverable endoscope 2B is sheathed with or unsheathed from an insertional part cover 11A, as shown in FIG. 34, a cover dilator 6 is used. The cover dilator 6 is identical to that shown in FIG. 28.

Figure 35:
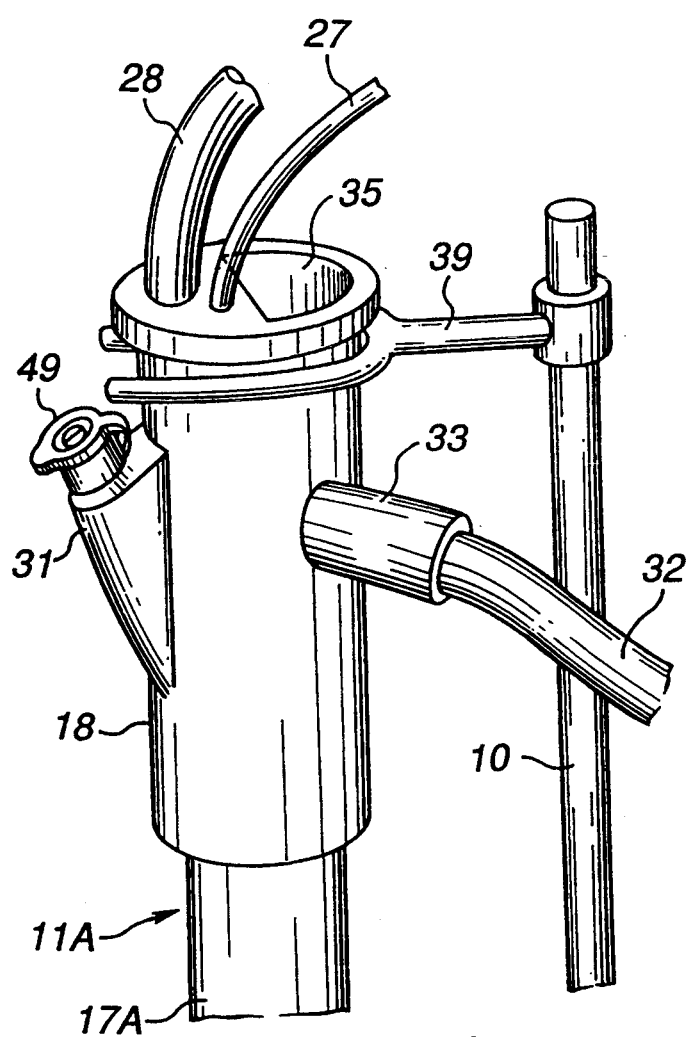
FIG. 35 is an oblique view of a holder of a cover holding instrument holding an insertional part cover.

For example, when the coverable endoscope 2B is inserted into the insertional part cover 11A, as shown in FIG. 35, a flange formed at the upper end of an operational part locked cap 18 is held with a semi-circular holder 39 attached to a cover holding instrument 10. Then, the insertional part 11B of the coverable endoscope 2B is inserted through an opening 35 on the top of the operational part locking cap 18. Thus, the coverable endoscope 2B can be inserted effortlessly.

Next, the operation of the twelfth embodiment will be described.

When the coverable endoscope 2B is sheathed with the insertional part cover 11A of a cover 2, as shown in FIG. 35, the semi-circular holder 39 attached to the cover holding instrument 10 is used to hold the flange formed at the upper end of the operational part locking cap 18.

Then, the terminal of a dilation tube 32 is coupled with the dilation tube cap 33. Thereby, air is fed from the cover dilator 6 to the endoscope insertion channel 34. The air leaks out through the opening 35 to the outside.

When the insertional part 11B of the coverable endoscope 2B is inserted through the opening 35, the projection 338 and notches 339 prevent the insertional part 11b from adhering to the wall of the endoscope insertion channel 34 (therefore, the endoscope insertion channel 34 will not be blocked). Air supplied to the dilation tube cap 33 can be routed to the endoscope insertional channel 34 via the notches 139. Then, an insertional part cover skin 17A forming the endoscope insertion channel 34 can be dilated, enabling smooth insertion of the insertional part 11B.

When insertion is completed, the terminal of the dilation tube 32 is decoupled from the dilation tube cap 33. Then, air leaks out through the dilation tube cap 33. The insertional part cover skin 17A shrinks due to its own elasticity (the outer diameter of the insertional part cover skin 17A shrinks). The outer surface, that is, the skin of the insertional part 11B substantially adheres to the inner surface of the insertional part cover skin 17A.

After the terminal of the dilation tube 32 is decoupled, a dilation tube cap cover 36 is attached to the dilation tube cap 33 in order to shield the dilation tube cap 33. This prevents the dilation tube cap 33 from being touched accidently with an operator's hand or a glove contaminated by applying the endoscope to a patient during endoscopic examination.

According to this embodiment, since the projection 338 is formed on the proximal opening of the dilation tube cap 33, the coverable endoscope 2B can be inserted or removed effortlessly.

In the twelfth embodiment, the dilation tube cap 33 may be formed by 180° in the radial direction apart from the forceps insertion cap 31; that is, may be formed on the opposite side of the forceps insertion cap 31. In this structure, since the dilation tube cap 33 and forceps insertion cap 31, which are projecting from an operational part locking cap 18, are opposed to each other, the operational part locking cap 18 can be ridded of dies easily. In other words, the operational part locking cap 18 can be molded easily.

Figure 36:
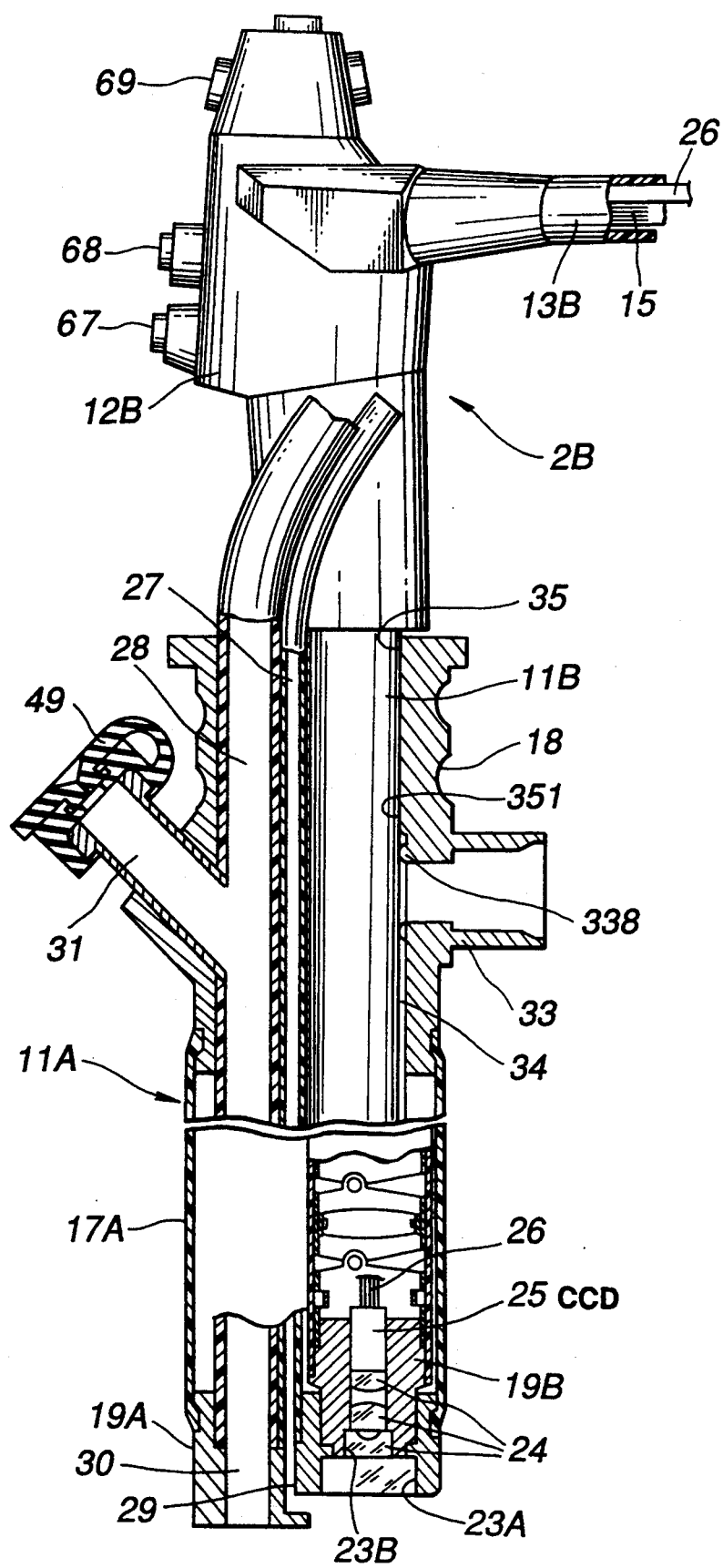
FIGS. 36 to 38 relate to a thirteenth embodiment of the present invention.

FIG. 36 shows a major portion of a covered endoscope 2 in the thirteenth embodiment of the present invention. In this embodiment, similarly to the twelfth embodiment, a projection 338 is formed on a proximal opening of a dilation tube cap 33. Furthermore, a projected wall 351 is formed in such a manner that an endoscope insertion channel 34 communicating with the opening will have a smaller cross-sectional area in its upper portion (on the side of an opening 35 through which an insertional part 11B is inserted) than in its lower portion (distal portion).

The other components are identical to those in the twelfth embodiment. This embodiment provides the same operation as the twelfth embodiment. Besides, since the upper portion of the endoscope insertion channel 34 has a smaller cross-sectional area than the lower portion thereof, when the insertional part 11B is inserted through the opening 35 so as to be sheathed with an insertional part cover 11A, the leakage of air through the upper portion can be minimized or eliminated. That is to say, the quantity of air leaking out toward the upper portion can be minimized or eliminated.

Supplied air can be routed toward the distal end of the endoscope insertion channel 34 more efficiently, which makes insertion and other operations easier.

Figure 37:
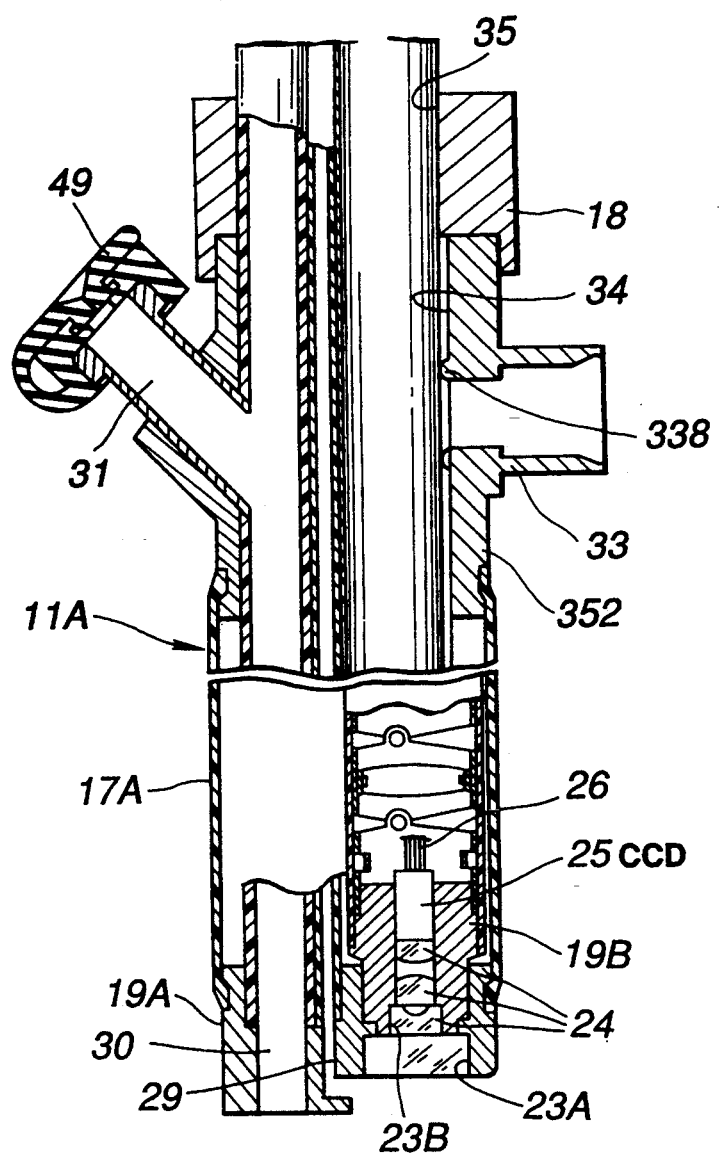

FIG. 37 shows a major portion of a covered endoscope 2 in the first variant of the thirteenth embodiment of the present invention. This variant has, similarly to the twelfth embodiment, a projection 338 on a proximal opening of a dilation tube cap 33. In this variant, a dilation tube cap 33 and a forceps insertion cap 31 are formed on a linker 352 for linking an operational part locking cap 18 with an insertional part cover skin 17A.

The endoscope insertion channel 34 has a smaller cross-sectional area at its end joining an opening of the operational part locking cap 18 than at its distal end. This variant operates similarly to the thirteenth embodiment.

In this variant, the operational part locking cap 18 can be molded with a different member independently of the dilation tube cap 33 and forceps insertion cap 31. The operational part locking cap 18, for example, can be molded with an elastic member. This facilitates sheathing efficiency.

Figure 38:
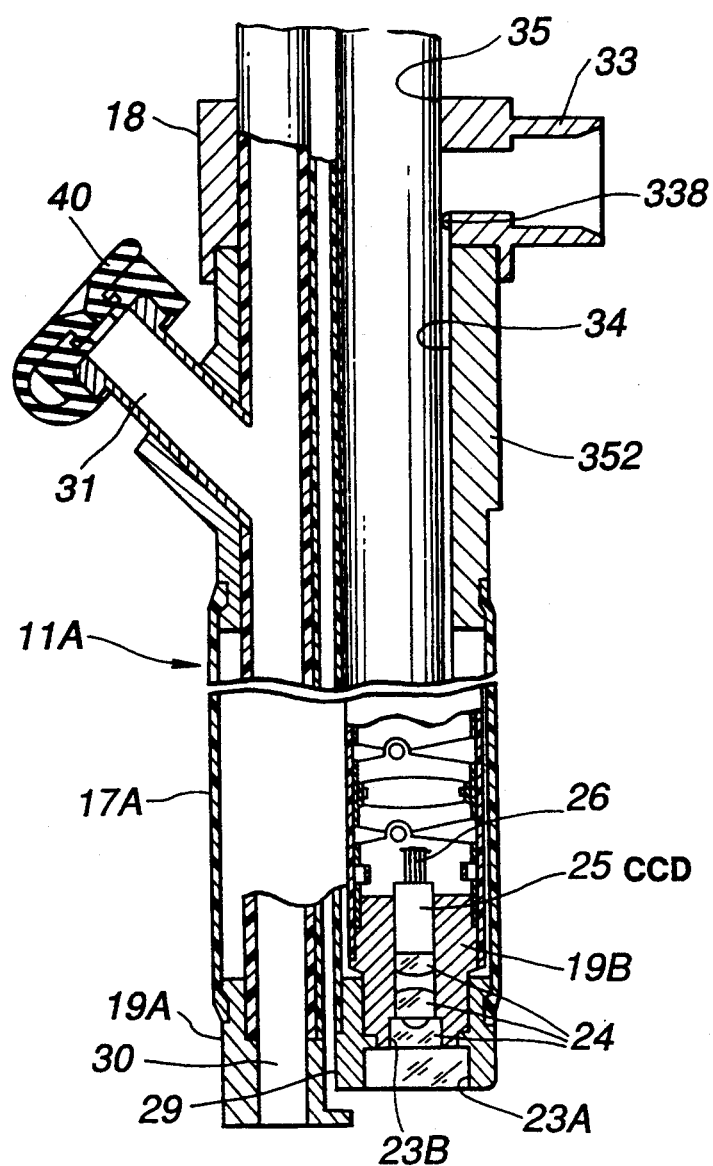

FIG. 38 shows a major portion of a covered endoscope 2 in the second variant of the thirteenth embodiment of the present invention. In this variant, similarly to the first embodiment, a projection 338 is formed on a proximal opening of a dilation tube cap 33 formed on an operational part locking cap 18. A forceps insertion cap 31 is formed on a linker 352 for linking the operational part locking cap 18 with an insertional part cover skin 17A.

The operational part locking cap 18 and linker 352 have the dilation tube cap 33 and forceps insertion cap 31 respectively. Molding these members is, therefore, simpler than molding a member having two projections.

A dent may be formed on the proximal opening of the dilation tube cap 33. The formation of the dent provides a gap capable of solving a problem that when a coverable endoscope 2B is inserted, the coverable endoscope 2B blocks the opening.

This structure prevents the coverable endoscope 2B from adhering to the opening and thus blocking the opening. Air can be easily fed to an endoscope insertion channel 34 via the dilation tube cap 33, which enables easy sheathing and unsheathing.

Furthermore, since the projection 338 in FIG. 31 is unnecessary and the proximal opening need not be deformed as shown in FIG. 36, the opening 35 of the endoscope insertion channel 34 can be molded easily.

The aforesaid eleventh to thirteenth embodiments can be combined partly or in any other manner to form different embodiments. For example, in the aforesaid embodiments, the forceps insertion cap and dilation tube cap may be separated from each other by 90° or more.

An endoscope used in conjunction with the cover 2A is not limited to the coverable endoscope 2B, but may be an endoscope which is used without the cover 2A; that is, used with the bare body.

As described above, according to the twelfth and thirteenth embodiments, a projection is formed in the vicinity of the proximal opening of a dilation tube cap communicating with an endoscope insertion channel. Thanks to the projection, when an insertional part is inserted, the inner wall of the endoscope insertion channel will not be pressed tightly to block a passage of air fed through the dilation tube cap into the endoscope insertion channel. The air passage can be reserved reliably, which permits easy insertion of the insertional part.

All the aforesaid embodiments can be combined partly or in any other manner to form different embodiments which will also belong to the present invention.

What is claimed is:

1. An endoscope cover-sheathed endoscope, comprising:
    an endoscope having an elongated insertional part that is adapted to be inserted into a living body and an operational part formed at the proximal end of said insertional part;
    an endoscope cover including an insertional part cover in which at least an endoscope insertion channel into which said insertional part is inserted is formed, and that sheaths said insertional part wherein said endoscope cover includes an operational cover for sheathing said operational part;
    a tube cap that is formed on said endoscope cover and communicates with said endoscope insertion channel in order to enable insertion or removal of said insertional part into or from said endoscope insertion channel, and with which the terminal of a tube for feeding air to said endoscope insertion channel is coupled; and
    a cap cover for shielding said tube cap wherein said cap cover is united with said operational cover.

2. An endoscope cover-sheathed endoscope, comprising:
    an endoscope having an elongated insertional part that is adapted to be inserted into a living body and an operational part formed at the proximal end of said insertional part;
    an endoscope cover including an insertional part cover having a rigid upper portion and in which at least an endoscope insertion channel into which said insertional part is inserted is formed, and that sheaths said insertional part wherein said endoscope cover has a tube cap that communicates with said endoscope insertion channel in order to enable insertion or removal of said insertional part into or from said endoscope insertion channel and with which the terminal of a tube for feeding air to said endoscope insertion channel is coupled;
    a holding instrument for holding said endoscope cover; and
    a holder attached to said holding instrument, for holding on to said rigid upper portion of said endoscope cover wherein said tube cap also functions as said holder.

3. An endoscope cover-sheathed endoscope, comprising:
    an endoscope having an elongated insertional part that is adapted to be inserted into a living body and an operational part formed at the proximal end of said insertional part;
    an endoscope cover including an insertional part cover in which at least an endoscope insertion channel into which said insertional part is inserted is formed, and that sheaths said insertional part;
    a cover dilator for feeding air to said endoscope insertion channel in order to enable insertion or removal of said insertional part into or from said endoscope insertion channel;
    a first connecting means located on said endoscope cover and a second connected means located on said cover dilator for connecting said endoscope cover and said cover dilator; and
    a joint means for joining said first connecting means and said second connecting means on a cover dilation side so that the first connecting means covers the second connecting means.

4. An endoscope cover-sheathed endoscope according to claim 3, wherein said connecting means is a tube.

* * * * *